(12) United States Patent
Lin

(10) Patent No.: US 11,357,555 B2
(45) Date of Patent: Jun. 14, 2022

(54) BONE FASTENING DEVICE HAVING PLATES AND SCREWS

(71) Applicant: Yu-Ju Lin, Kaohsiung (TW)

(72) Inventor: Yu-Ju Lin, Kaohsiung (TW)

( * ) Notice: Subject to any disclaimer, the term of this patent is extended or adjusted under 35 U.S.C. 154(b) by 83 days.

(21) Appl. No.: 17/103,980

(22) Filed: Nov. 25, 2020

(65) Prior Publication Data

US 2021/0077166 A1   Mar. 18, 2021

(51) Int. Cl.
*A61B 17/80* (2006.01)
*A61B 17/86* (2006.01)

(52) U.S. Cl.
CPC ...... *A61B 17/8052* (2013.01); *A61B 17/8023* (2013.01); *A61B 17/8615* (2013.01); *A61B 17/8625* (2013.01)

(58) Field of Classification Search
CPC ............ A61B 17/8052; A61B 17/8057; A61B 17/8023
See application file for complete search history.

(56) References Cited

U.S. PATENT DOCUMENTS

| | | | |
|---|---|---|---|
| 2003/0212399 A1* | 11/2003 | Dinh ................... | A61B 17/7059 606/279 |
| 2018/0235671 A1* | 8/2018 | Jackson, III .......... | A61F 2/4455 |
| 2021/0137573 A1* | 5/2021 | Jackson, III ....... | A61B 17/8023 |

* cited by examiner

*Primary Examiner* — Olivia C Chang

(57) ABSTRACT

A bone fastening device includes a ready-to-assemble plate assembly including hingedly secured first, second, third, and fourth plates, first insertion members, second insertion members, a plurality of upper half adjustment members, and a plurality of lower half adjustment members; and a plurality of screws configured to drive through the first, second, third, and fourth plates into the broken bone.

5 Claims, 21 Drawing Sheets

BONE FASTENING DEVICE HAVING PLATES AND SCREWS

BACKGROUND OF THE INVENTION

1. Field of the Invention

The invention relates to bone fastening devices and more particularly to a device including ready-to-assemble plates hingedly secured together and screws for driving through the plates into a broken bone to secure the plates to the bone.

2. Description of Related Art

Conventionally, an orthopedic cast, or simply cast, is a shell, frequently made from plaster, that encases a limb to stabilize and hold anatomical structures (e.g., a broken bone) in place until healing is confirmed. As the medical technologies evolve, many doctors may use plates and screws as a replacement of the orthopedic cast for stabilize and hold the broken bone in place because the combination of plates and screws are more advantageous than the orthopedic cast in terms of bone dislocation prevention and shorter healing time.

There are a wide variety of plates for securing to a broken bone commercially available. These plates are designed based on bones in different portions of the body. However, lengths of bones of one person are different from that of another person. Thus, many different sizes of the plate are available even for a single type of plate. This means a hospital has to buy and store a wide variety of plates. Inevitably, it bears a great financial burden on the hospital.

Thus, the need for improvement still exists.

SUMMARY OF THE INVENTION

It is therefore a first object of the invention to provide a bone fastening device adapted to secure to one of a plurality of different shapes of bones.

It is a second object of the invention to provide a bone fastening device capable of adjusting length to secure to one of a plurality of different lengths of bones.

To achieve above and other objects of the invention, the invention provides a bone fastening device comprising a ready-to-assemble plate assembly including a first plate, a second plate, a third plate, a fourth plate, first insertion members, second insertion members, a plurality of upper half adjustment members, and a plurality of lower half adjustment members; and a plurality of screws wherein the first plate includes a plurality of first direction adjustment holes on a top, the first direction adjustment hole having a truncated conic shape; a first groove on a bottom passing through the first direction adjustment holes and being perpendicular thereto; and a first hinge section at a first side and having a knuckle, a threaded hole through the knuckle, and a trough aligned with the threaded hole and communicating therewith; the second plate and the first plate are joined; the second plate includes a plurality of second direction adjustment holes on a top, the second direction adjustment hole having a truncated conic shape; a second groove on a bottom passing through the second direction adjustment holes and being perpendicular thereto; a second hinge section at a second side and having a first knuckle, a first threaded hole through the first knuckle, and a first trough aligned with the first threaded hole and communicating therewith; and a third hinge section at a first side and having a second knuckle, a second threaded hole through the second knuckle, and a second trough aligned with the second threaded hole and communicating therewith; the third plate and the second plate are joined; the third plate includes a plurality of third direction adjustment holes on a top, the third direction adjustment hole having a truncated conic shape; a third groove on a bottom passing through the third direction adjustment holes and being perpendicular thereto; a fourth hinge section at a second side and having a first knuckle, a first threaded hole through the first knuckle, and a first trough aligned with the first threaded hole and communicating therewith; and a fifth hinge section at a first side and having a second knuckle and a second trough at the second side and passing through the second knuckle; the fourth plate and the third plate are joined; the fourth plate includes a plurality of fourth direction adjustment holes on a top, the third direction adjustment hole having a truncated conic shape; two parallel fourth grooves on a bottom each passing through one of the fourth direction adjustment holes and being perpendicular thereto; and a sixth hinge section at a second side and having a knuckle, a threaded hole through the knuckle, and a trough aligned with the threaded hole and communicating therewith; the first insertion members are inserted into the first groove and the second groove respectively; the first insertion member includes a plurality of first insertion adjustment holes corresponding to the first direction adjustment holes and the second direction adjustment holes respectively; and the first insertion adjustment hole has a truncated conic shape; the second insertion members are inserted into the third groove and the fourth grooves respectively; the second insertion member includes a plurality of second insertion adjustment holes corresponding to the third direction adjustment hole and the fourth direction adjustment holes respectively; and the second insertion adjustment hole has a truncated conic shape; the upper half adjustment members are disposed in the first direction adjustment holes, the second direction adjustment holes, the third direction adjustment hole, and the fourth direction adjustment holes respectively; the upper half adjustment member is configured to fit in the truncated conic shape inner surface of each of the first direction adjustment hole, the second direction adjustment hole, the third direction adjustment hole, and the fourth direction adjustment hole; and the upper half adjustment member includes a threaded hole; the lower half adjustment member includes a through hole having a diameter less than that of the threaded hole of the upper half adjustment member; and an outer surface of the lower half adjustment member is shaped as an inverted truncated cone to allow the lower half adjustment member to dispose in the first insertion adjustment hole or the second insertion adjustment holes; and the screw includes a head having a socket and first external threads; a shank having second external threads and a concave tip; and a cylindrical positioning section between the head, the shank positioning section having a diameter equal to a diameter of the lower half adjustment member; and the head is threadedly fastened in the threaded hole of the lower half adjustment member.

Preferably, a width of the third plate is less than that of the second plate.

Preferably, a width of the fourth plate is equal to that of the third plate.

Preferably, the upper half adjustment member includes a plurality of threaded positioning holes.

Preferably, further comprises a plurality of positioning bolts disposed in the threaded positioning holes respectively.

The above and other objects, features and advantages of the invention will become apparent from the following detailed description taken with the accompanying drawings.

DETAILED DESCRIPTION OF THE INVENTION

Referring to FIGS. 1 to 30, a bone fastening device 1 in accordance with the invention is shown.

Figure 1:
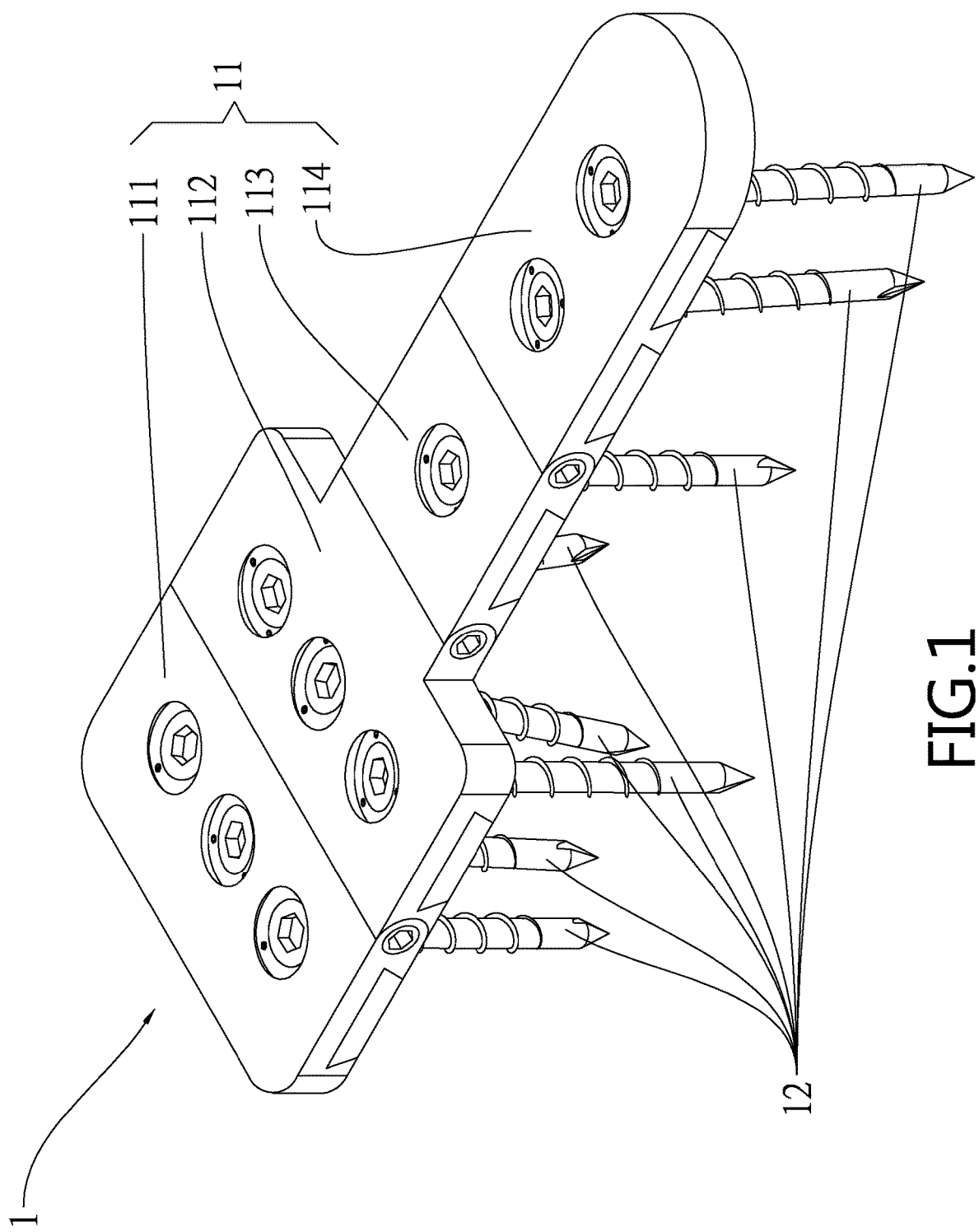
FIG. 1 is a perspective view of a bone fastening device according to the invention.
Figure 2:
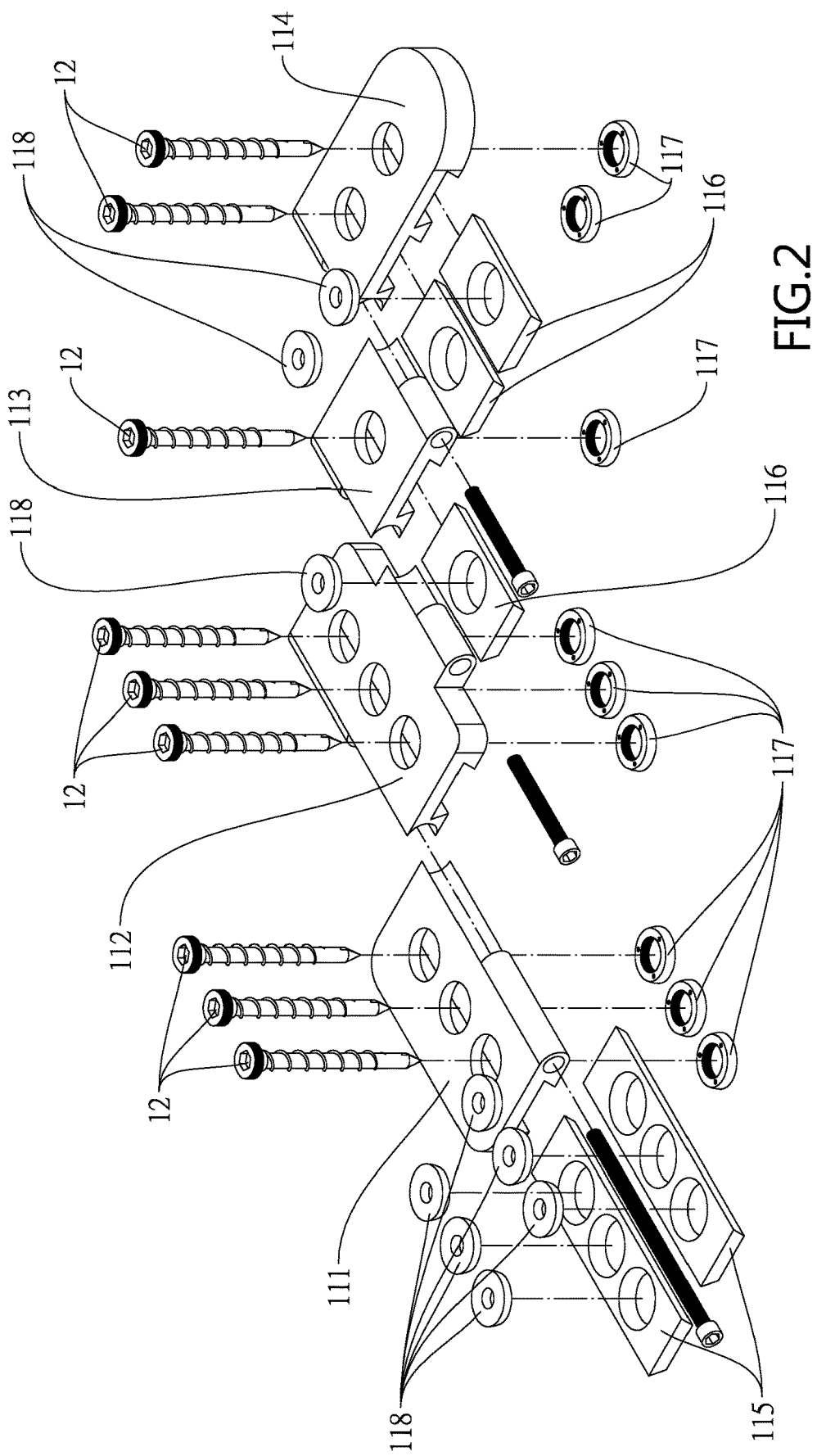
FIG. 2 is an exploded view of the bone fastening device.

As shown in FIGS. 1 and 2 specifically, the bone fastening device 1 comprises a ready-to-assemble plate assembly 11 and a plurality of screws 12. The ready-to-assemble plate assembly 11 includes a first plate 111, a second plate 112, a third plate 113, a fourth plate 114, first insertion members 115, second insertion members 116, a plurality of upper half adjustment members 117 and a plurality of lower half adjustment members 118.

Figure 3:
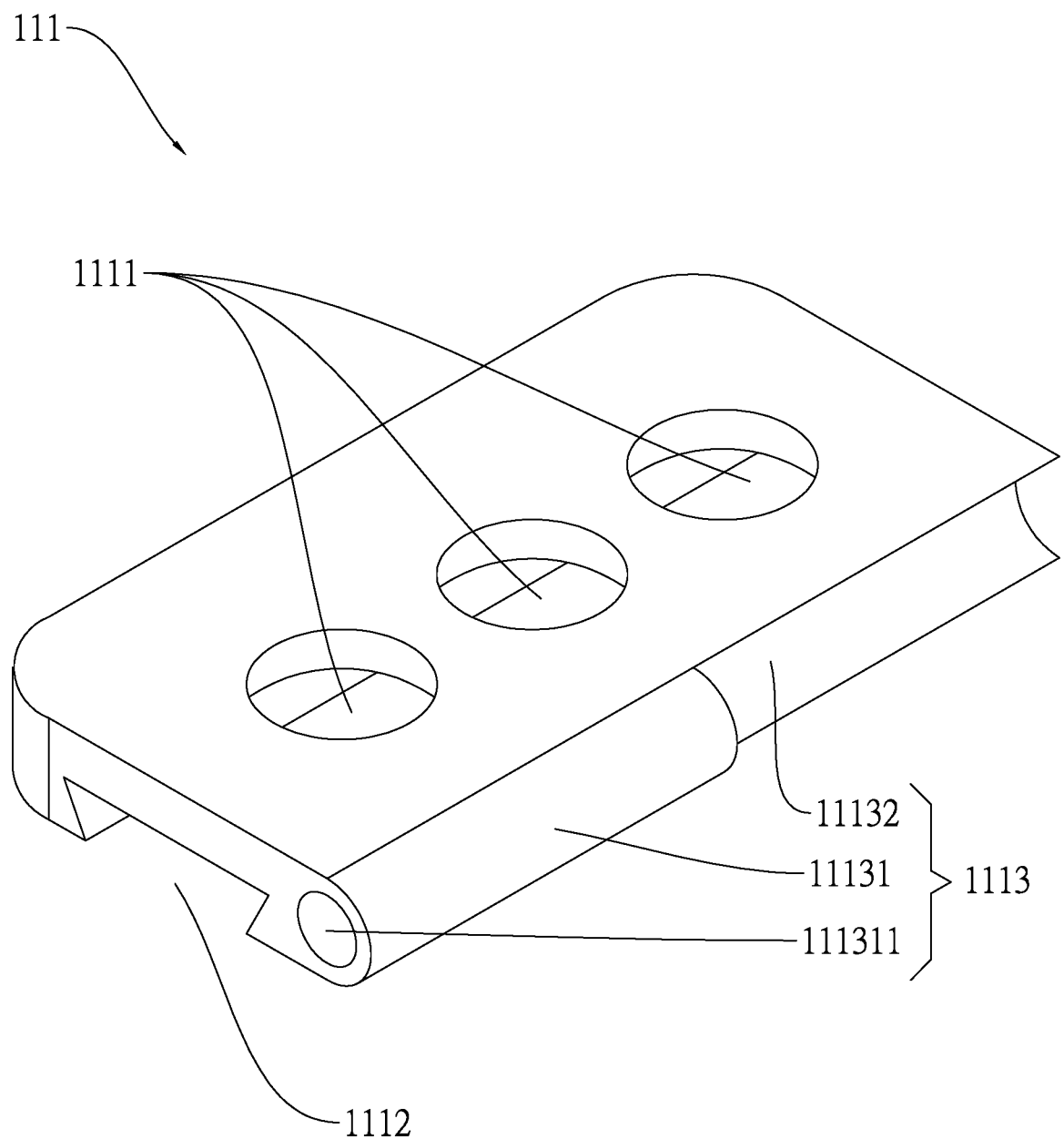
FIG. 3 is a perspective view of the first plate.

As shown in FIG. 3 specifically, the first plate 111 includes a plurality of first direction adjustment holes 1111 on a top, the first direction adjustment hole 1111 having a truncated conic shape; a first groove 1112 on a bottom passing through the first direction adjustment holes 1111 and being perpendicular thereto; and a first hinge section 1113 at a first side and having a knuckle 11131, a threaded hole 111311 through the knuckle 11131, and a trough 11132 aligned with the threaded hole 111311 and communicating therewith.

Figure 4:
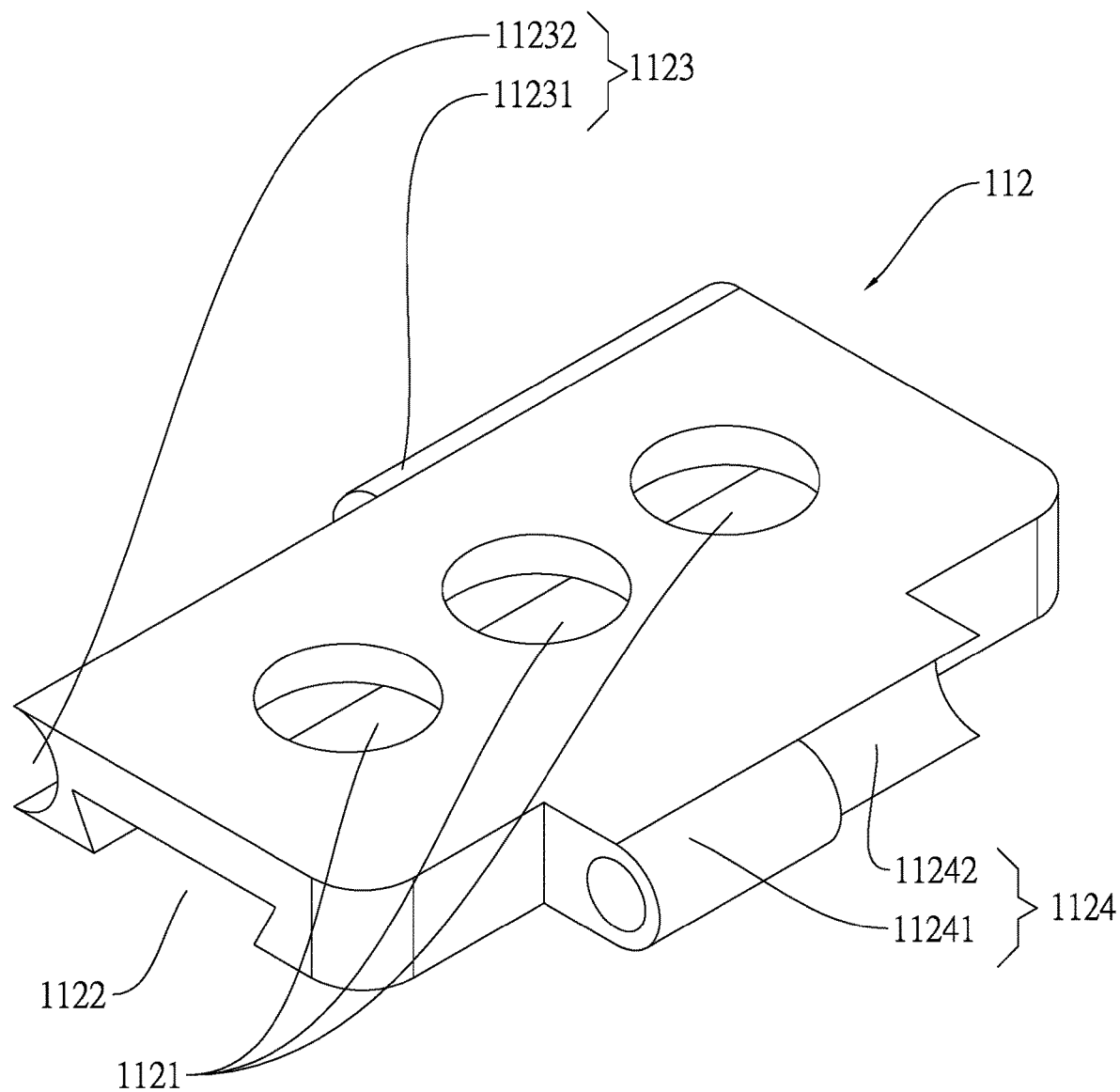
FIG. 4 is a perspective view of the second plate.
Figure 5:
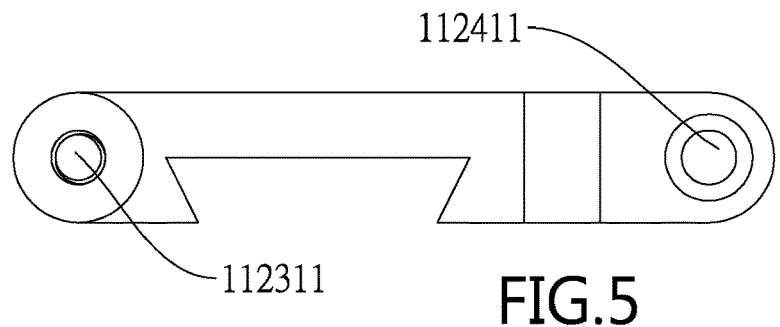
FIG. 5 is a front view of the second plate.

As shown in FIGS. 4 and 5 specifically, the second plate 112 and the first plate 111 are joined. The second plate 112 includes a plurality of second direction adjustment holes 1121 on a top, the second direction adjustment hole 1121 having a truncated conic shape; a second groove 1122 on a bottom passing through the second direction adjustment holes 1121 and being perpendicular thereto; a second hinge section 1123 at a second side and having a knuckle 11231, a threaded hole 112311 through the knuckle 11231, and a trough 11232 aligned with the threaded hole 112311 and communicating therewith; and a third hinge section 1124 at a first side and having a knuckle 11241, a threaded hole 112411 through the knuckle 11241, and a trough 11242 aligned with the threaded hole 112411 and communicating therewith.

Figure 6:
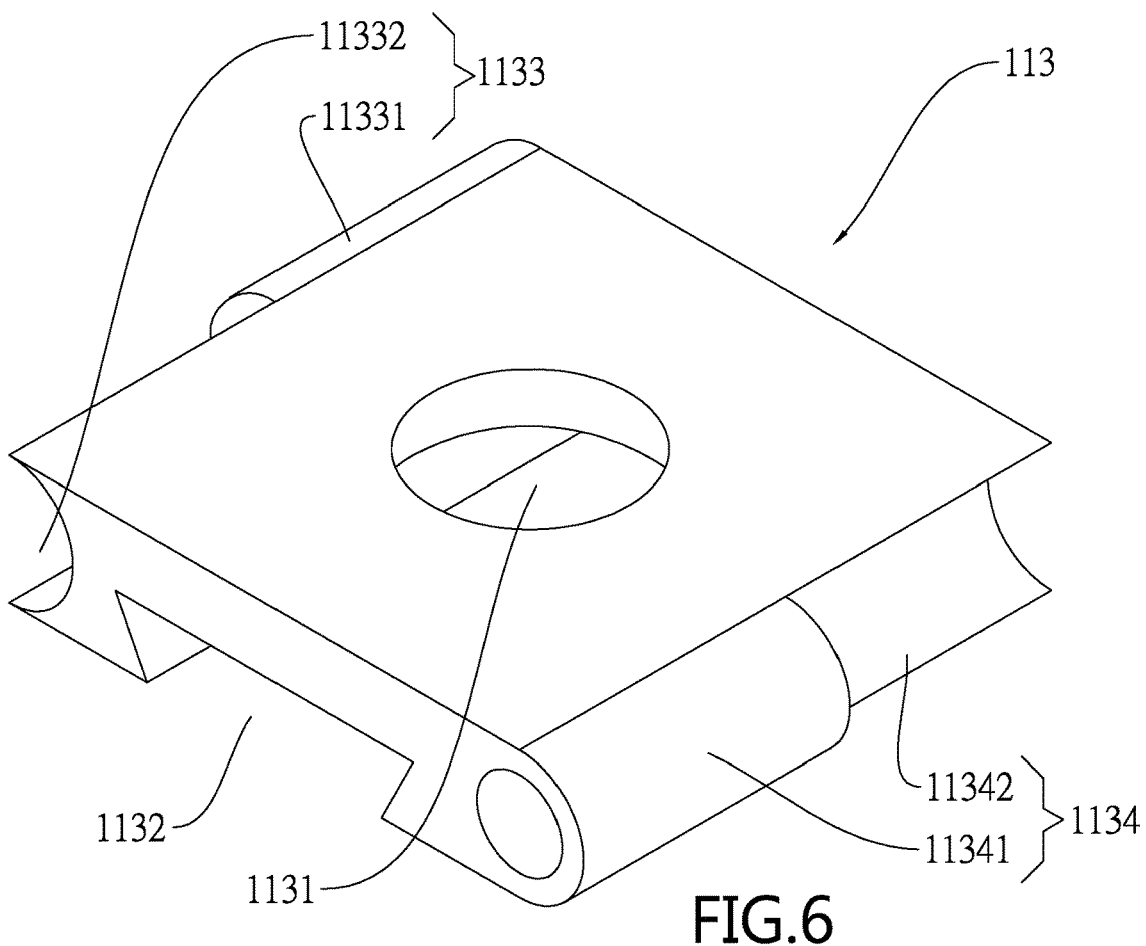
FIG. 6 is a perspective view of the third plate.
Figure 7:
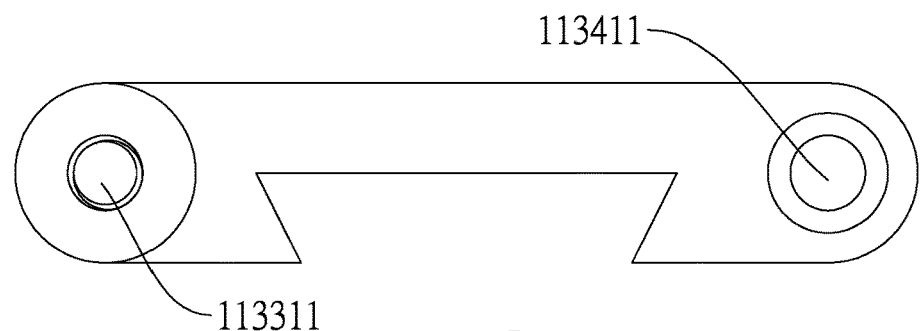
FIG. 7 is a front view of the third plate.

As shown in FIGS. 6 and 7 specifically, the third plate 113 and the second plate 112 are joined. The third plate 113 includes a plurality of third direction adjustment holes 1131 on a top, the third direction adjustment hole 1131 having a truncated conic shape; a third groove 1132 on a bottom passing through the third direction adjustment holes 1131 and being perpendicular thereto; a fourth hinge section 1133 at a second side and having a knuckle 11331, a threaded hole 113311 through the knuckle 11331, and a trough 11332 aligned with the threaded hole 113311 and communicating therewith; and a fifth hinge section 1134 at a first side and having a knuckle 11341 and a trough 11342 at the second side and passing through the knuckle 11341. The fourth hinge section 1133 and the third hinge section 1124 are joined. The knuckle 11331 is aligned with the trough 11242. The knuckle 11241 is aligned with the trough 11332.

Figure 9:
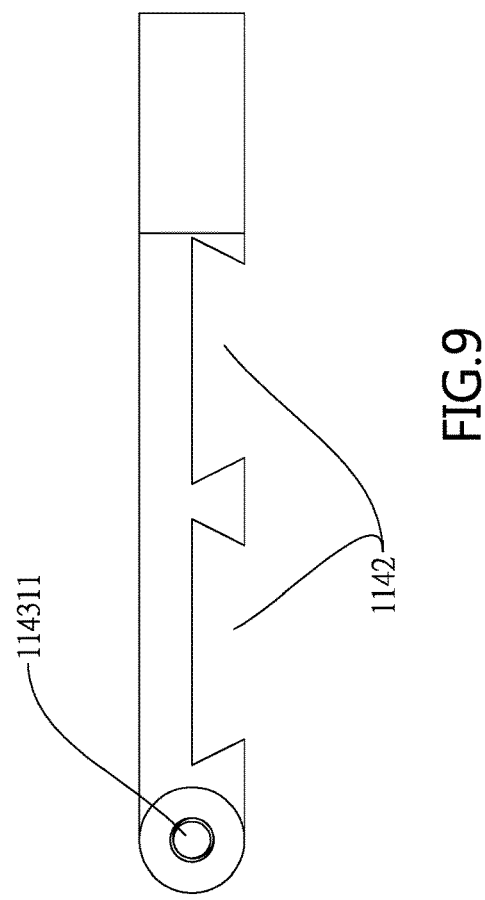
FIG. 9 is a front view of the fourth plate.
Figure 8:
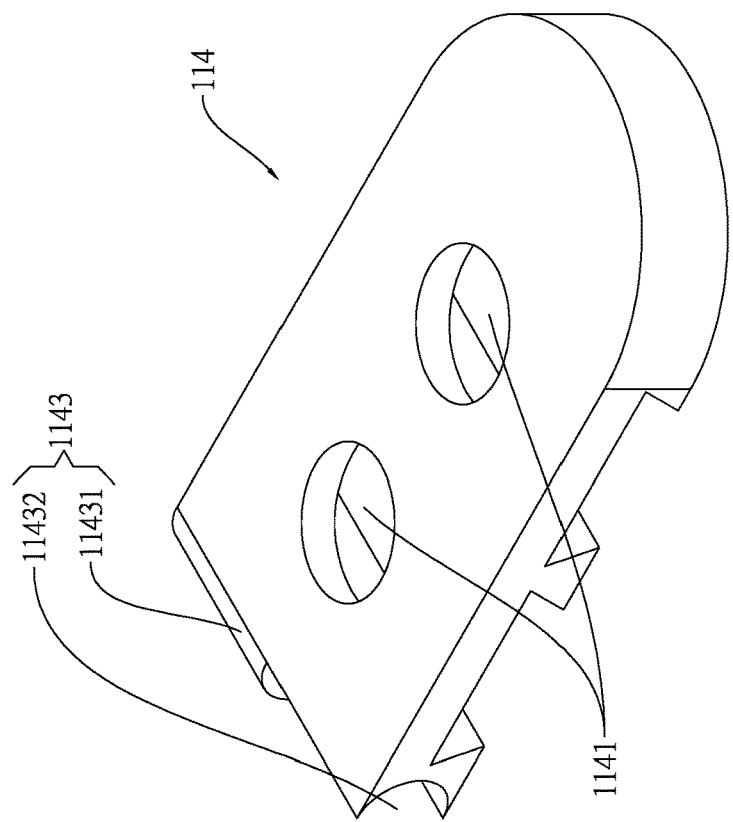
FIG. 8 is a perspective view of the fourth plate.

As shown in FIGS. 8 and 9 specifically, the fourth plate 114 and the third plate 113 are joined. The fourth plate 114 includes a plurality of fourth direction adjustment holes 1141 on a top, the third direction adjustment hole 1141 having a truncated conic shape; two parallel fourth grooves 1142 on a bottom each passing through one of the fourth direction adjustment holes 1141 and being perpendicular thereto; and a sixth hinge section 1143 at a second side and having a knuckle 11431, a threaded hole 114311 through the knuckle 11431, and a trough 11432 aligned with the threaded hole 114311 and communicating therewith.. The knuckle 11431 is aligned with the trough 11342. The knuckle 11341 is aligned with the trough 11432.

Figure 10:
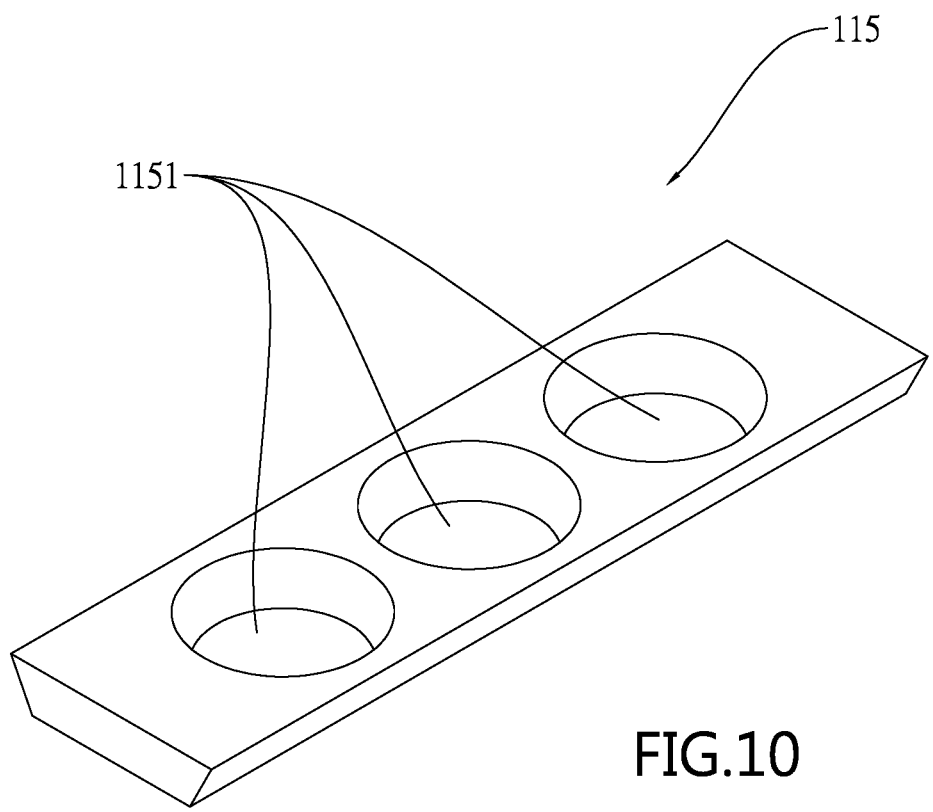
FIG. 10 is a perspective view of the first insertion member.

As shown in FIG. 10 specifically, the first insertion members 115 are inserted into the first groove 1112 and the second groove 1122 respectively. The first insertion member 15 includes a plurality of first insertion adjustment holes 1151 corresponding to the first direction adjustment holes 1111 and the second direction adjustment holes 1121 respectively. The first insertion adjustment hole 1151 has a truncated conic shape.

Figure 11:
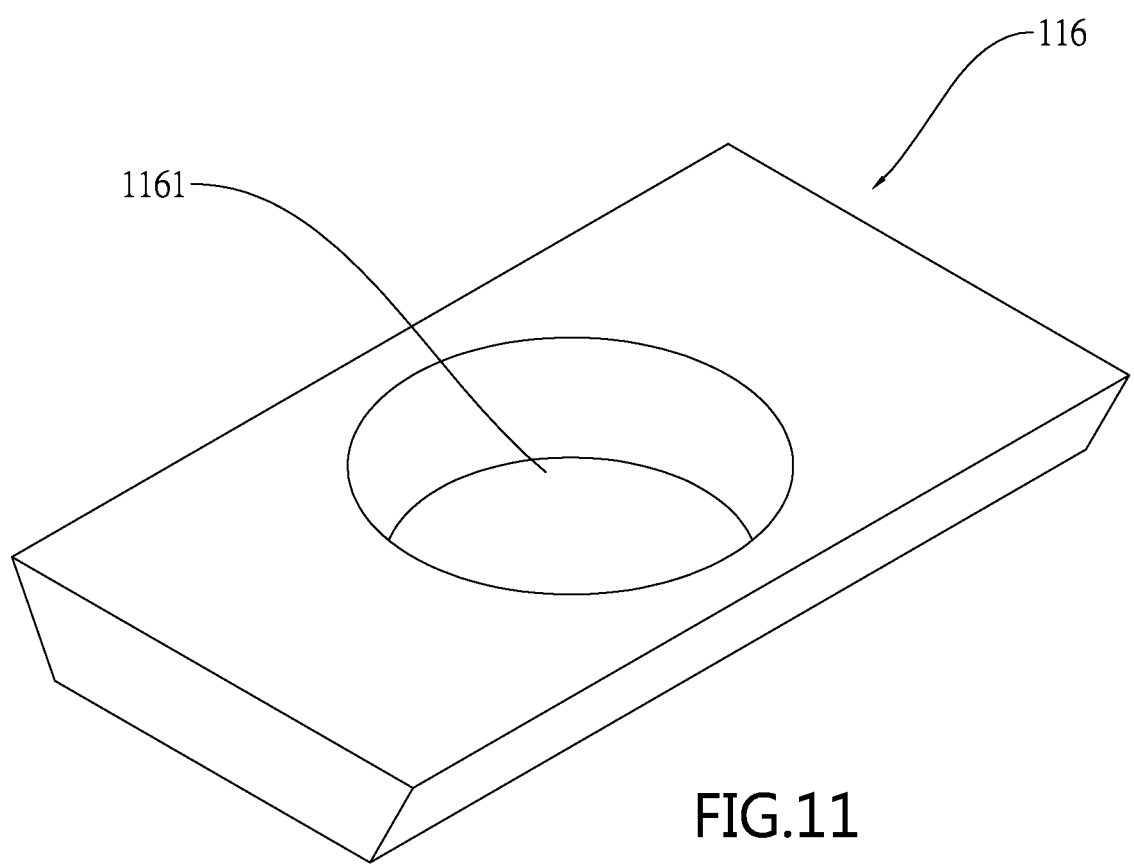
FIG. 11 is a perspective view of the second insertion member.

As shown in FIG. 11 specifically, the second insertion members 116 are inserted into the third groove 1132 and the fourth grooves 1142 respectively. The second insertion member 16 includes a plurality of second insertion adjustment holes 1161 corresponding to the third direction adjustment hole 1131 and the fourth direction adjustment holes 1141 respectively. The second insertion adjustment hole 1161 has a truncated conic shape.

Figure 12:
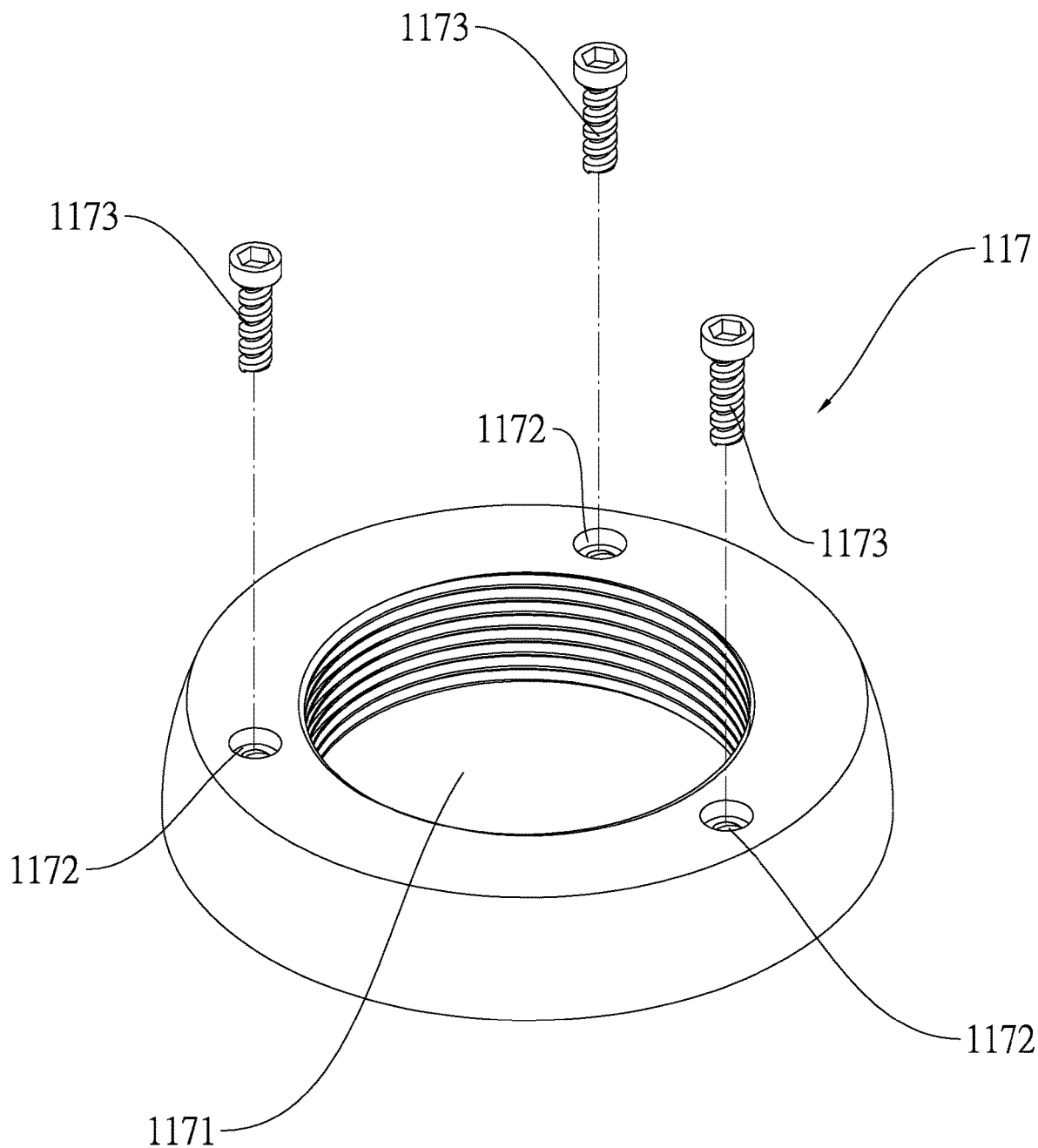
FIG. 12 is an exploded view of the upper half adjustment member.
Figure 13:
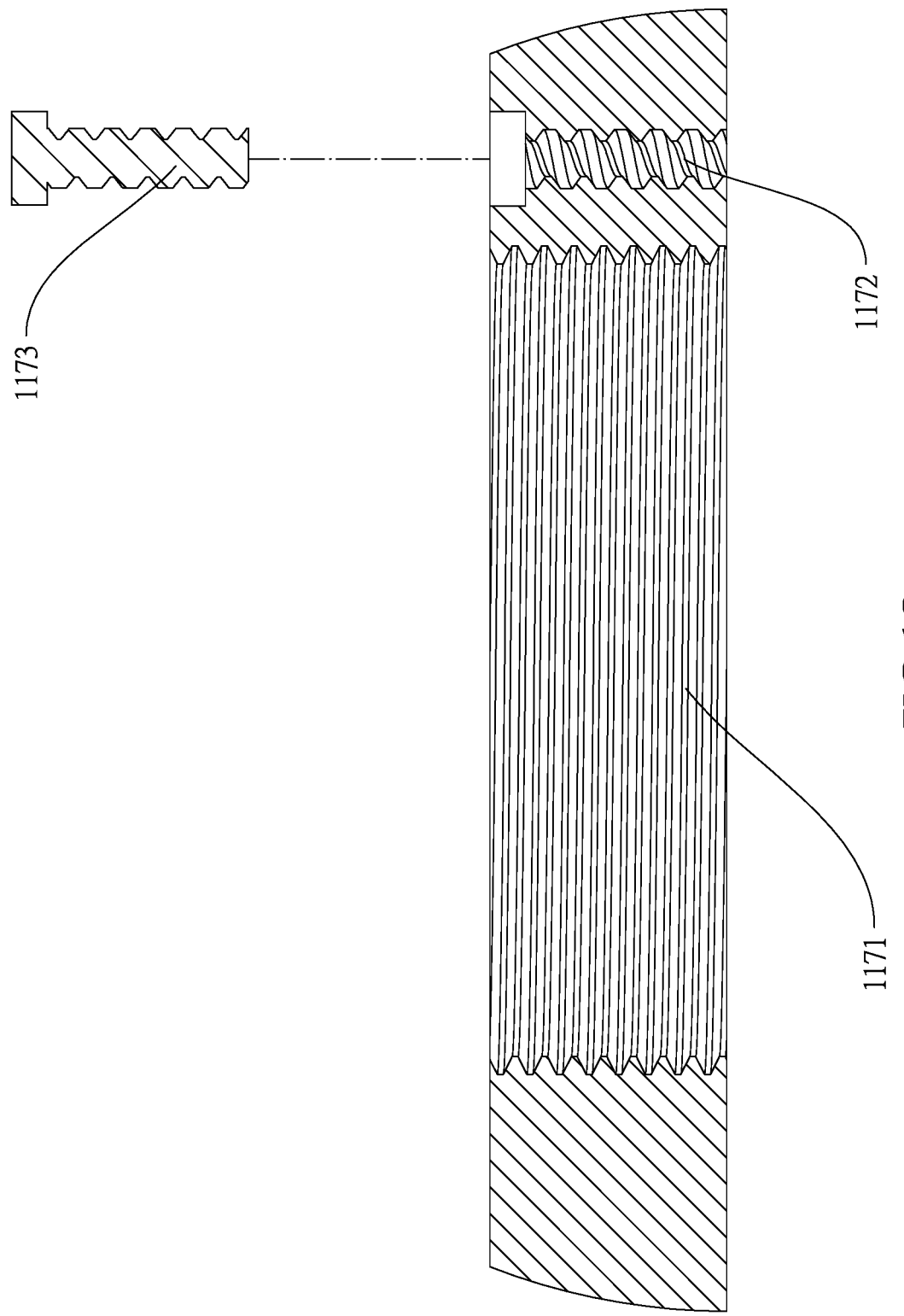
FIG. 13 is a longitudinal sectional view of the upper half adjustment member.

As shown in FIGS. 12 and 13 specifically, the upper half adjustment members 117 are disposed in the first direction adjustment holes 1111, the second direction adjustment holes 1121, the third direction adjustment hole 1131 and the fourth direction adjustment holes 1141 respectively. The upper half adjustment member 117 is adapted to fit in the truncated conic shape inner surface of each of the first direction adjustment hole 1111, the second direction adjustment hole 1121, the third direction adjustment hole 1131 and the fourth direction adjustment hole 1141 and includes a threaded hole 1171, a plurality of threaded positioning holes 1172 and a plurality of positioning bolts 1173 disposed in the threaded positioning holes 1172 respectively.

Figure 14:
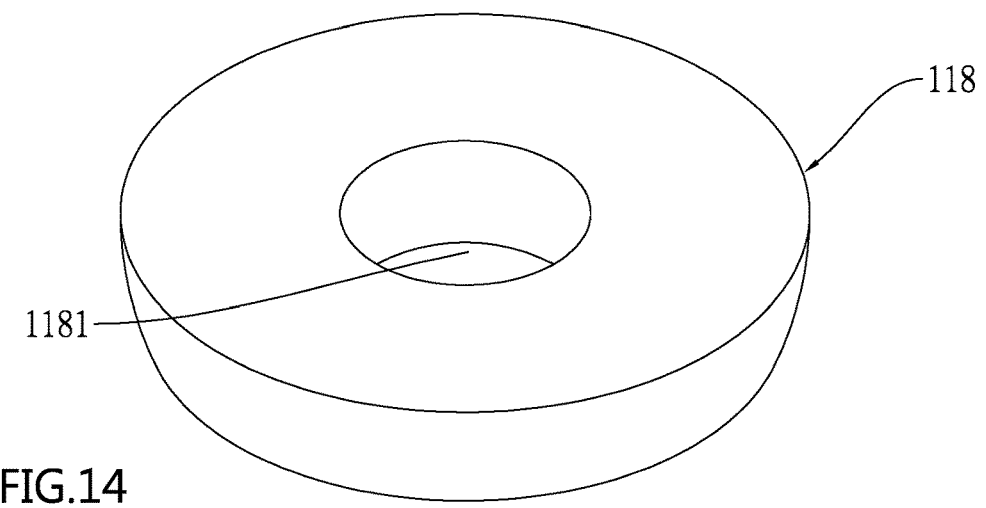
FIG. 14 is a perspective view of the lower half adjustment member.

As shown in FIG. 14 specifically, the lower half adjustment member 118 includes a through hole 1181 having a diameter less than that of the threaded hole 1171, An outer surface of the lower half adjustment member 118 is shaped as an inverted truncated cone so as to allow the lower half adjustment member 118 to dispose in the first insertion adjustment hole 1151 or the second insertion adjustment holes 1161.

Figure 15:
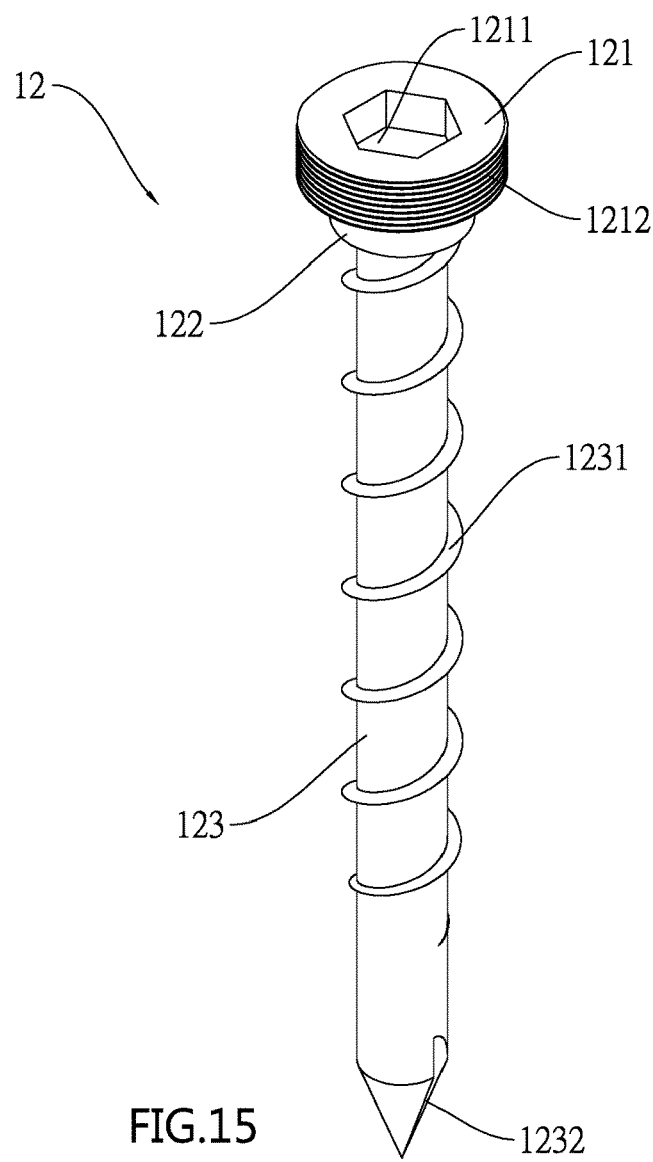
FIG. 15 is a perspective view of the screw.
Figure 16:
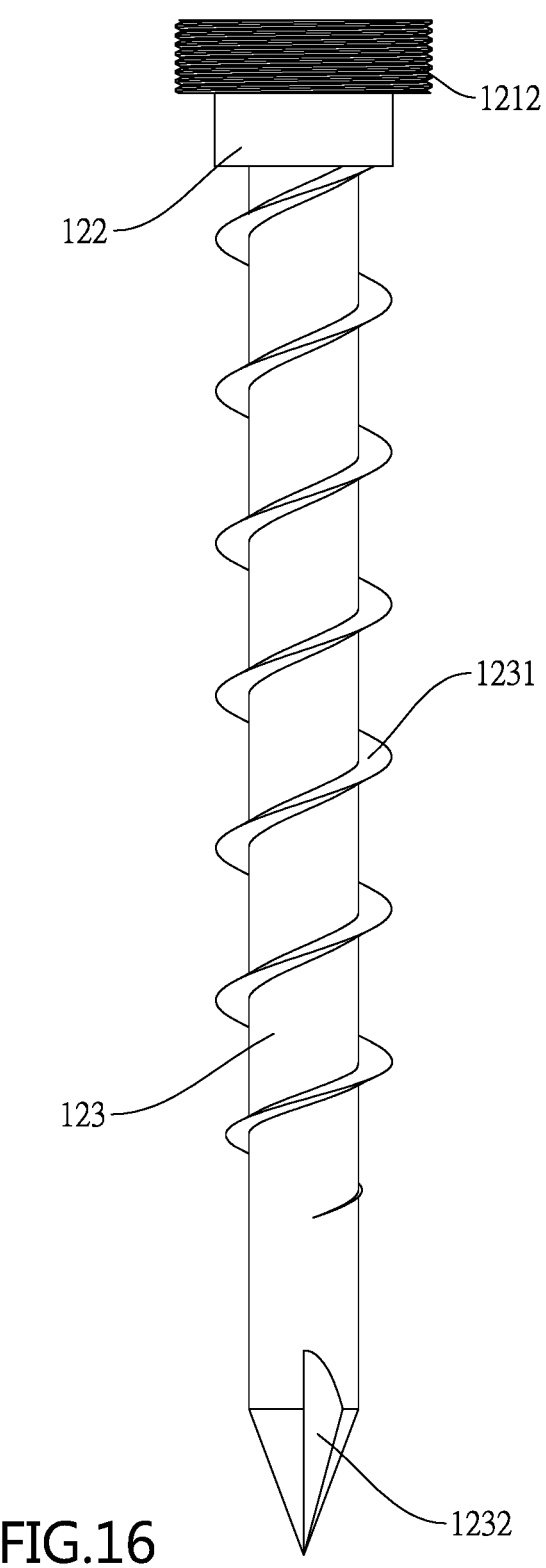
FIG. 16 is a side elevation of the screw.
Figure 17:
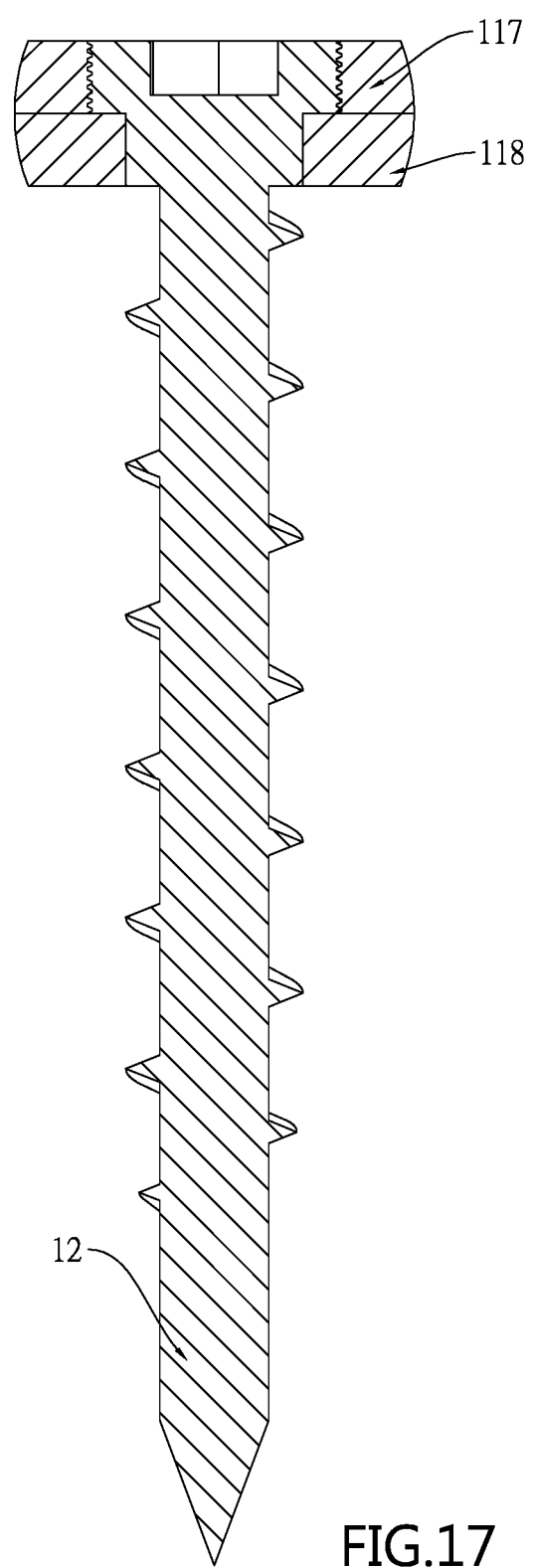
FIG. 17 is a longitudinal sectional view of the screw with mounted upper half adjustment member and lower half adjustment member.
Figure 18:
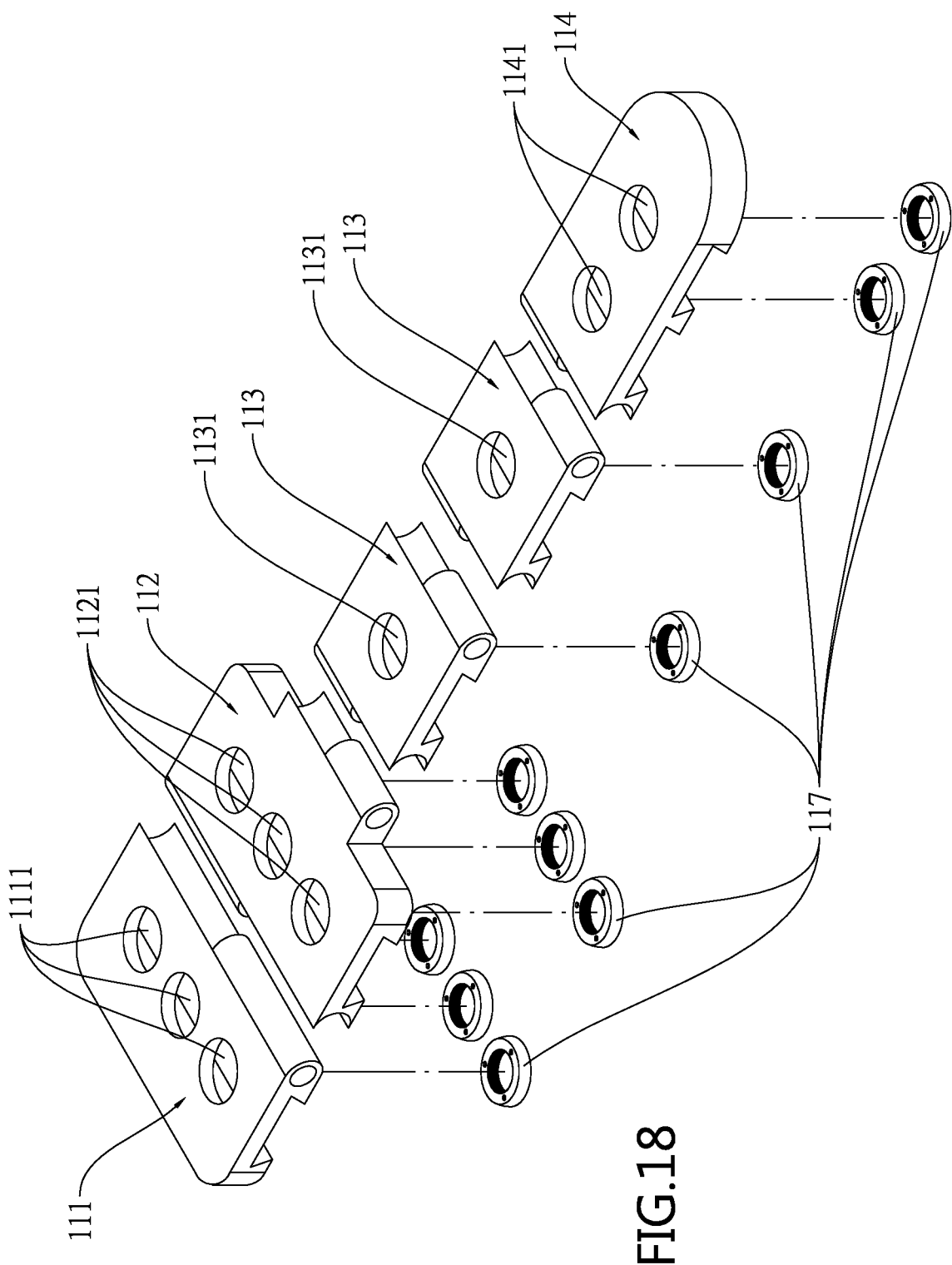
FIG. 18 schematically depicts a first step of installing the bone fastening device.
Figure 19:
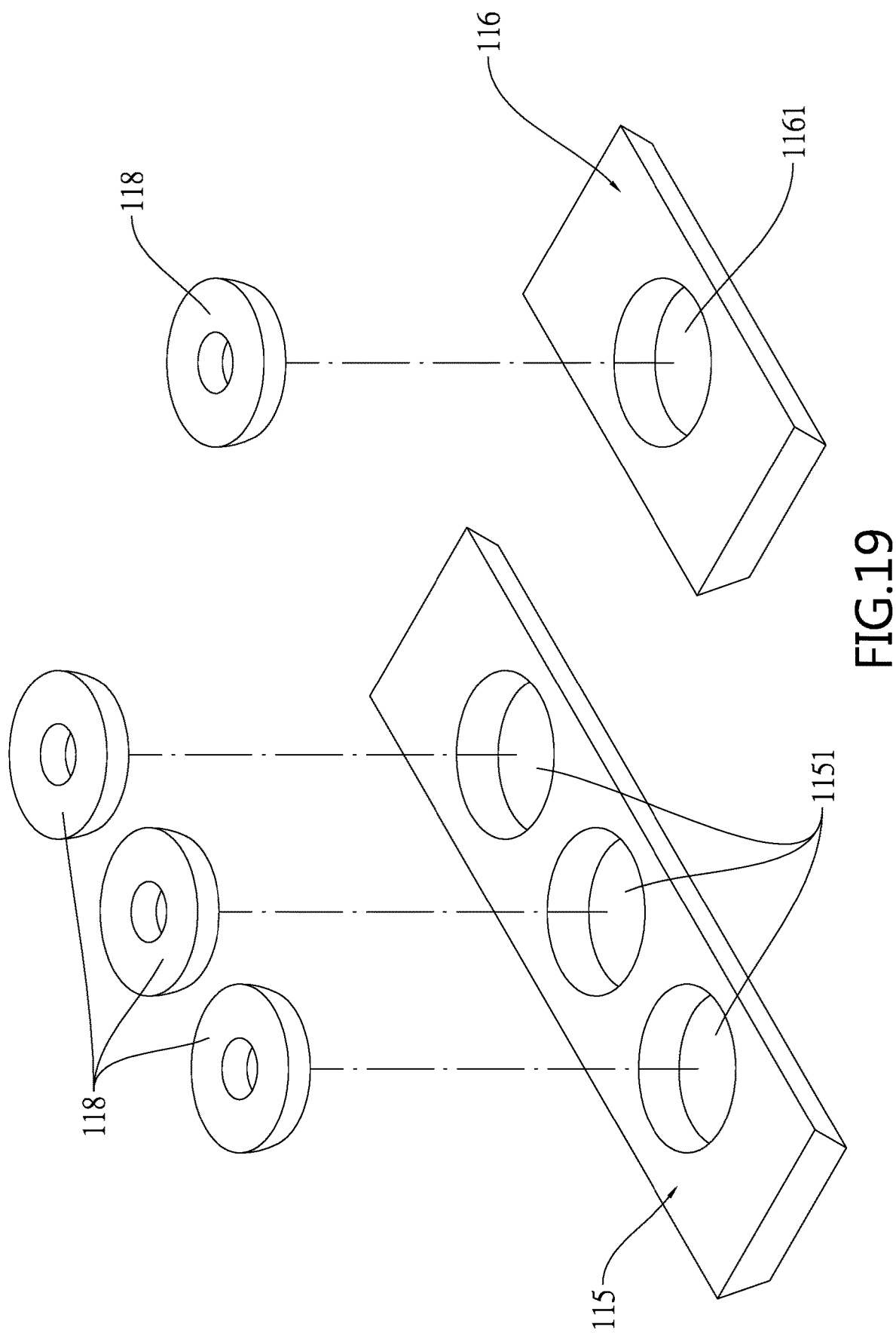
FIG. 19 schematically depicts a second step of installing the bone fastening device.
Figure 20:
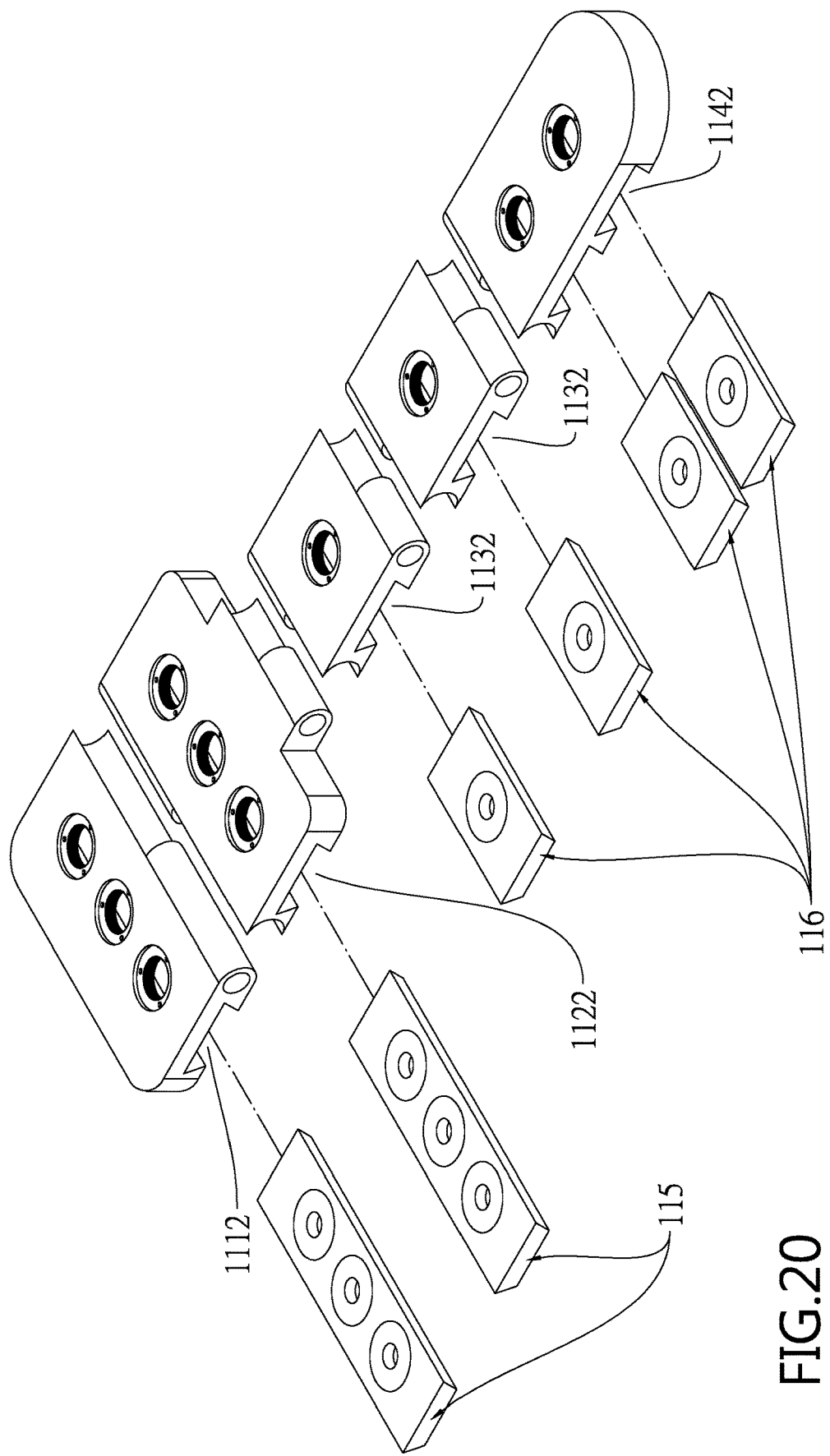
FIG. 20 schematically depicts a third step of installing the bone fastening device.
Figure 21:
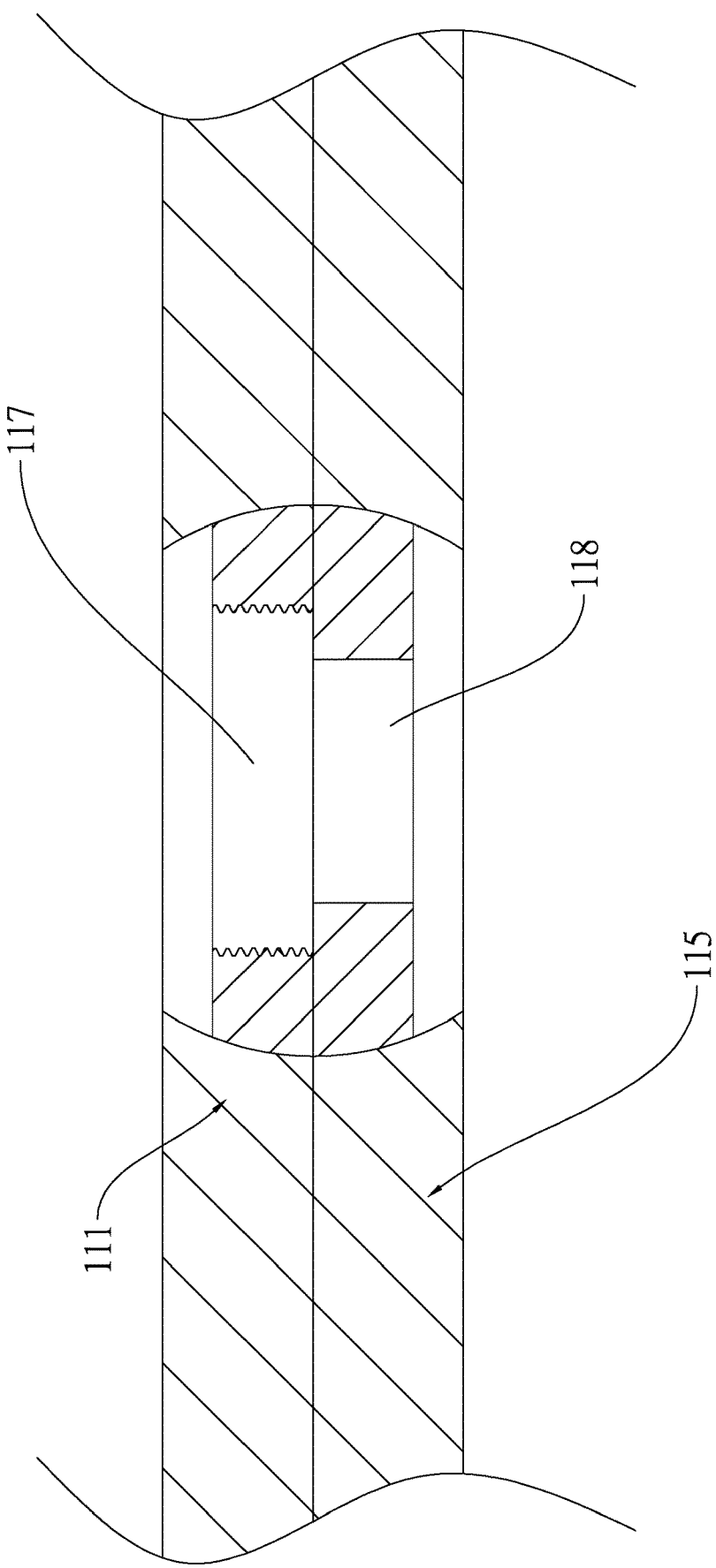
FIG. 21 schematically depicts a fourth step of installing the bone fastening device.

As shown in FIGS. 15 to 17 in conjunction with FIGS. 9 and 10 specifically, the screw 12 includes a head 121 having a hexagonal socket 1211 and first external threads 1212; a shank 123 having second external threads 1231 and a concave tip 1232; and a positioning section 122 between the head 121 and the shank 123. The head 121 is threadedly fastened in the threaded hole 1171. The positioning section 122 is cylindrical and has a diameter equal to a diameter of the lower half adjustment member 118. The second external threads 1231 have a diameter equal to or slightly less than a diameter of the through hole 1181. The positioning section 122 is engaged with the through hole 1181 when the screw 12 is driven to secure the upper half adjustment member 117 and the lower half adjustment member 118 together.

As shown in FIGS. 18 to 21 in conjunction with FIGS. 3, 4, 6 and 8 specifically, an assembly of the ready-to-assemble plate assembly 11 is discussed below. The number of the third plate 113 can be increased depending on location of the bone fracture and other conditions so that the total length of the ready-to-assemble plate assembly 11 can cover the bone fracture. The upper half adjustment members 117 are fitted in the first direction adjustment holes 1111, the second direction adjustment holes 1121, the third direction adjustment hole 1131 and the fourth direction adjustment holes 1141 respectively. Next, the lower half adjustment members 118 are fitted in the first insertion adjustment holes 1151 and the second insertion adjustment holes 1161 respectively. Next, the first insertion members 115 are inserted into the first groove 1112 and the second groove 1122 respectively. The second insertion members 116 are inserted into the third groove 1132 and the fourth grooves 1142 respectively. After the first insertion member 115 has been inserted into the first groove 1112, the first direction adjustment hole 1111 is aligned with the first insertion adjustment hole 1151 to form a spherical space having both top and bottom truncated. After the first insertion member 115 has been inserted into the second groove 1122, the first direction adjustment hole 1111 is aligned with the second insertion adjustment hole 1161 to form a spherical space having both top and bottom truncated. After the second insertion member 116 has been inserted into the third groove 1132, the second direction adjustment hole 1121 is aligned with a third insertion adjustment hole (not numbered) to form a spherical space having both top and bottom truncated. After the second insertion member 116 has been inserted into the fourth groove 1142, the second direction adjustment hole 1121 is aligned with a fourth insertion adjustment hole (not numbered) to form a spherical space having both top and bottom truncated. After the first insertion members 115 have been inserted into the first plate 111 and thea second plate 112 respectively, and the second insertion members 116 have been inserted into the third plate 113 and the fourth plate 114 respectively, the above upper half adjustment member 117 and its corresponding lower half adjustment member 118 are aligned to form a spherical space having both top and bottom truncated. But a thickness of the spherical space having both top and bottom truncated is less than that of a total thickness of all of the spherical space.

Figure 22:
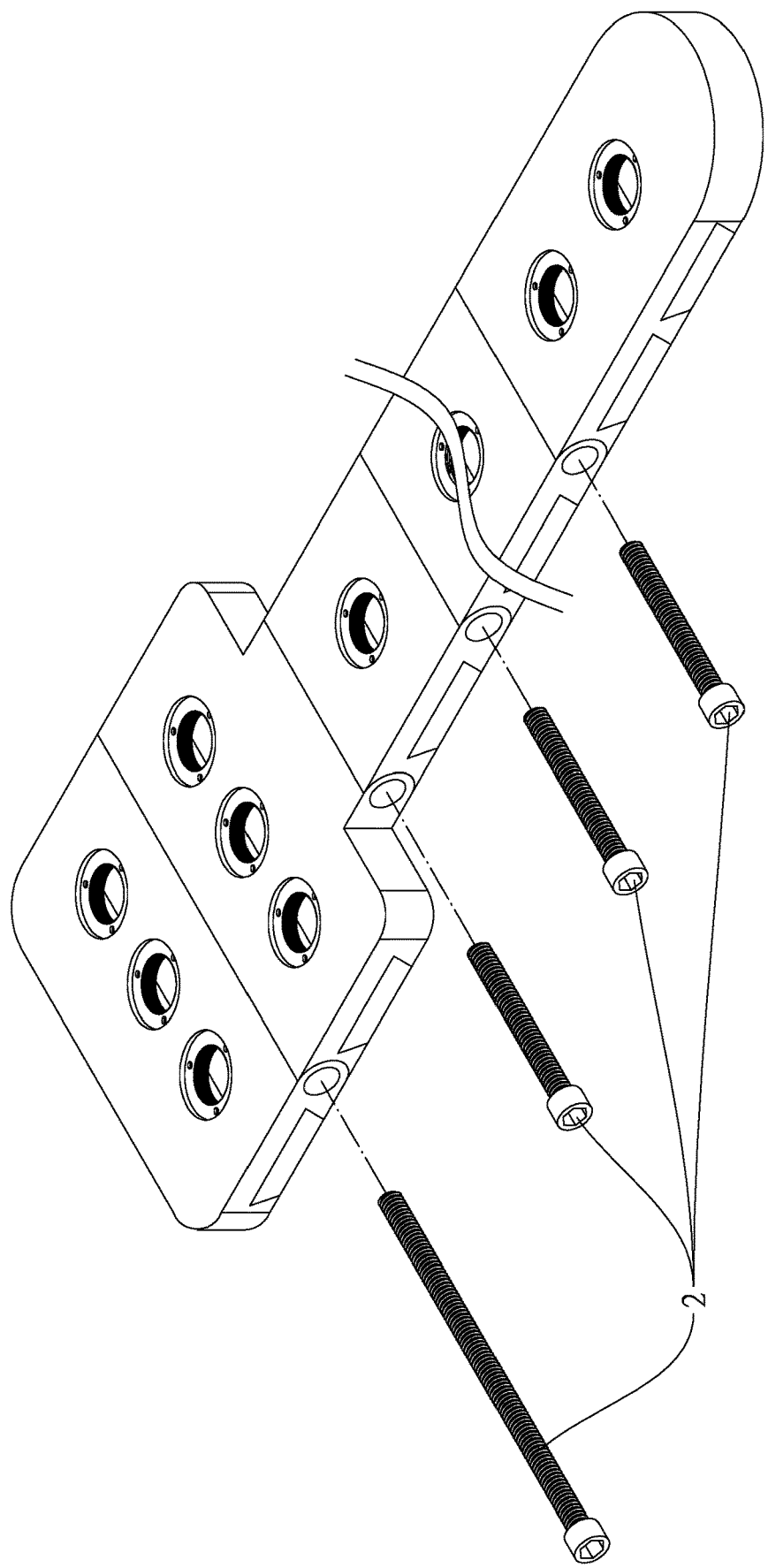
FIG. 22 schematically depicts a fifth step of installing the bone fastening device.
Figure 23:
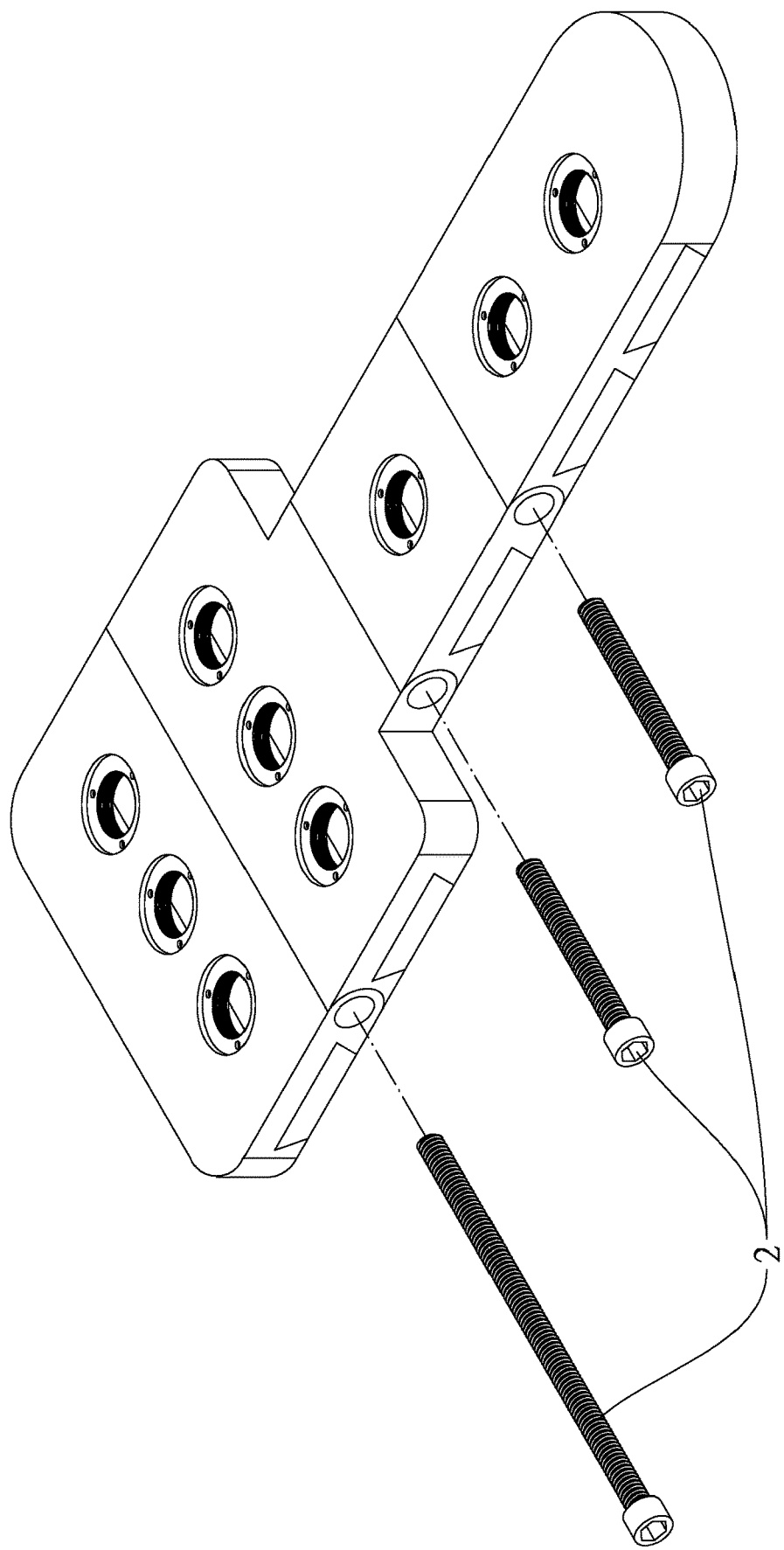
FIG. 23 schematically depicts a sixth step of installing the bone fastening device.
Figure 24:
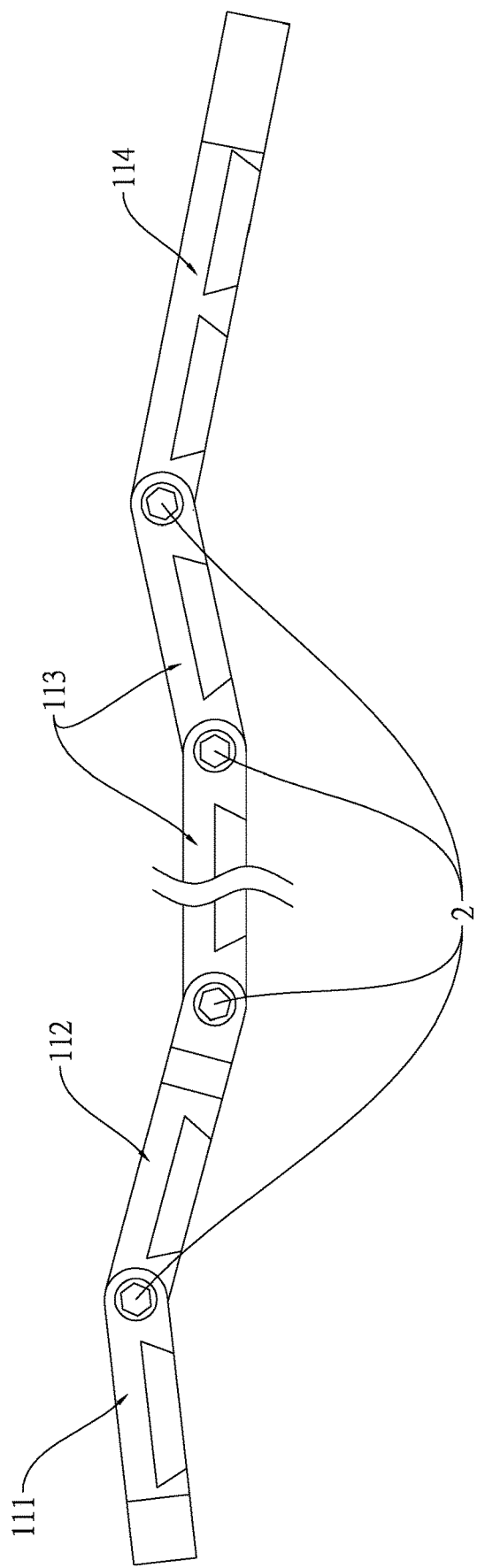
FIG. 24 schematically depicts a seventh step of installing the bone fastening device.
Figure 25:
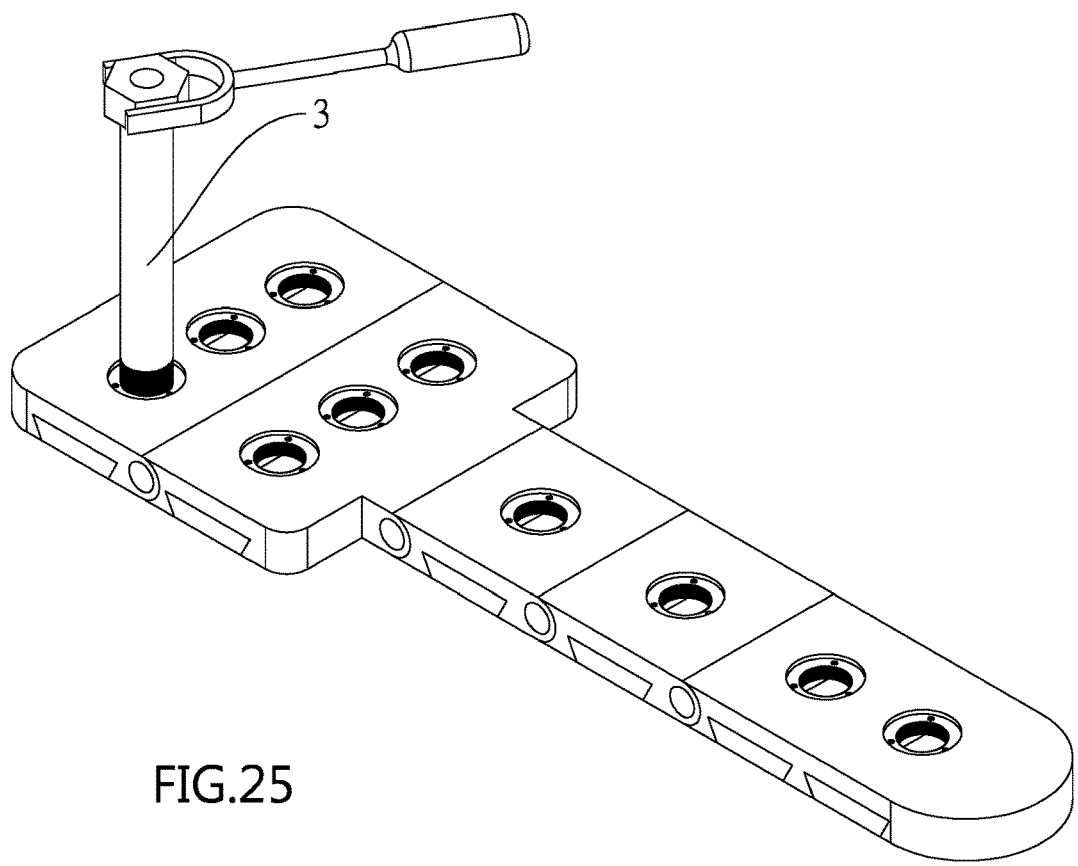
FIG. 25 schematically depicts an eighth step of installing the bone fastening device.
Figure 26:
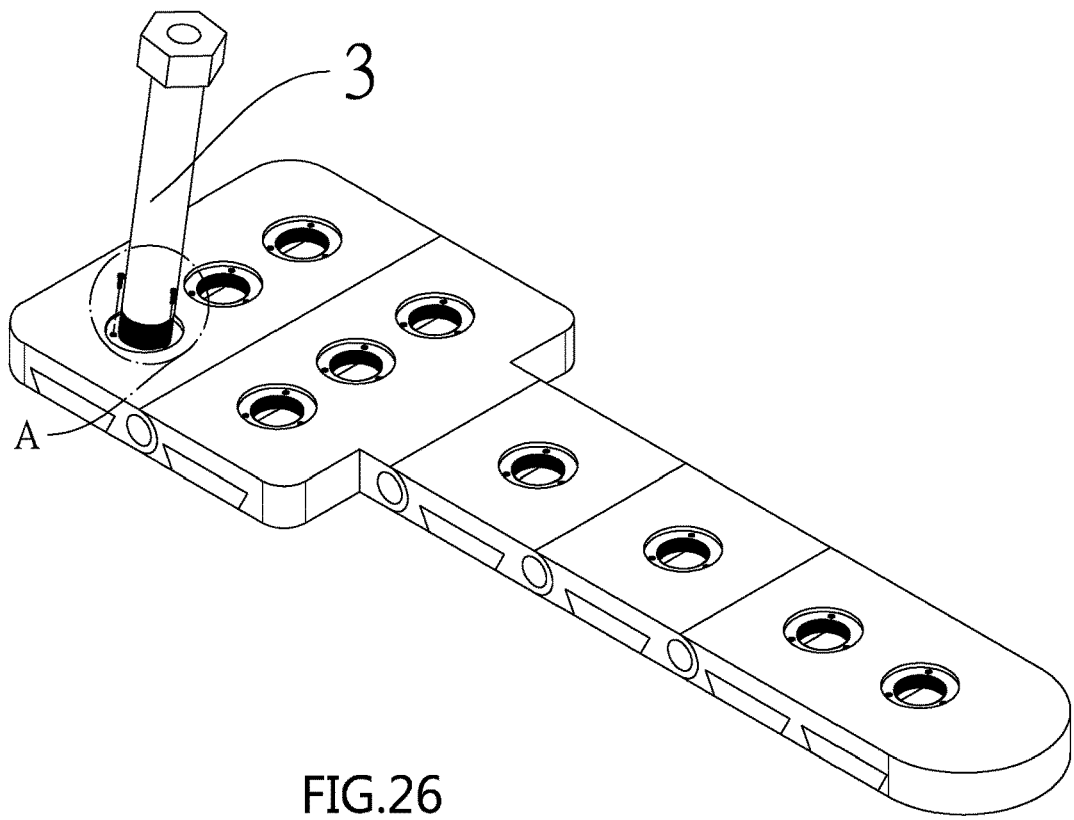
FIG. 26 schematically depicts a ninth step of installing the bone fastening device.
Figure 27:
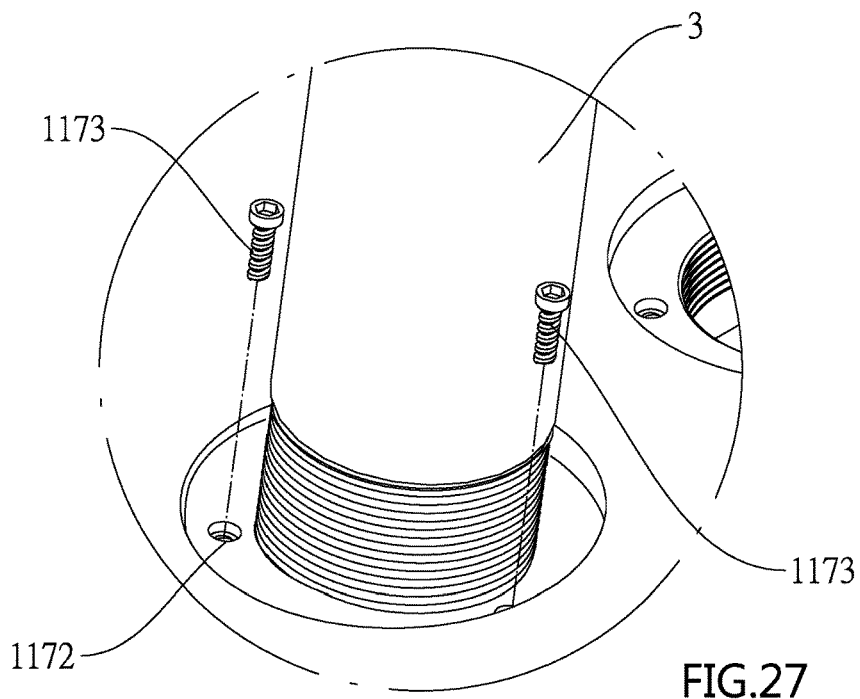
FIG. 27 is a detailed view of the area in circle A of FIG. 26.
Figure 28:
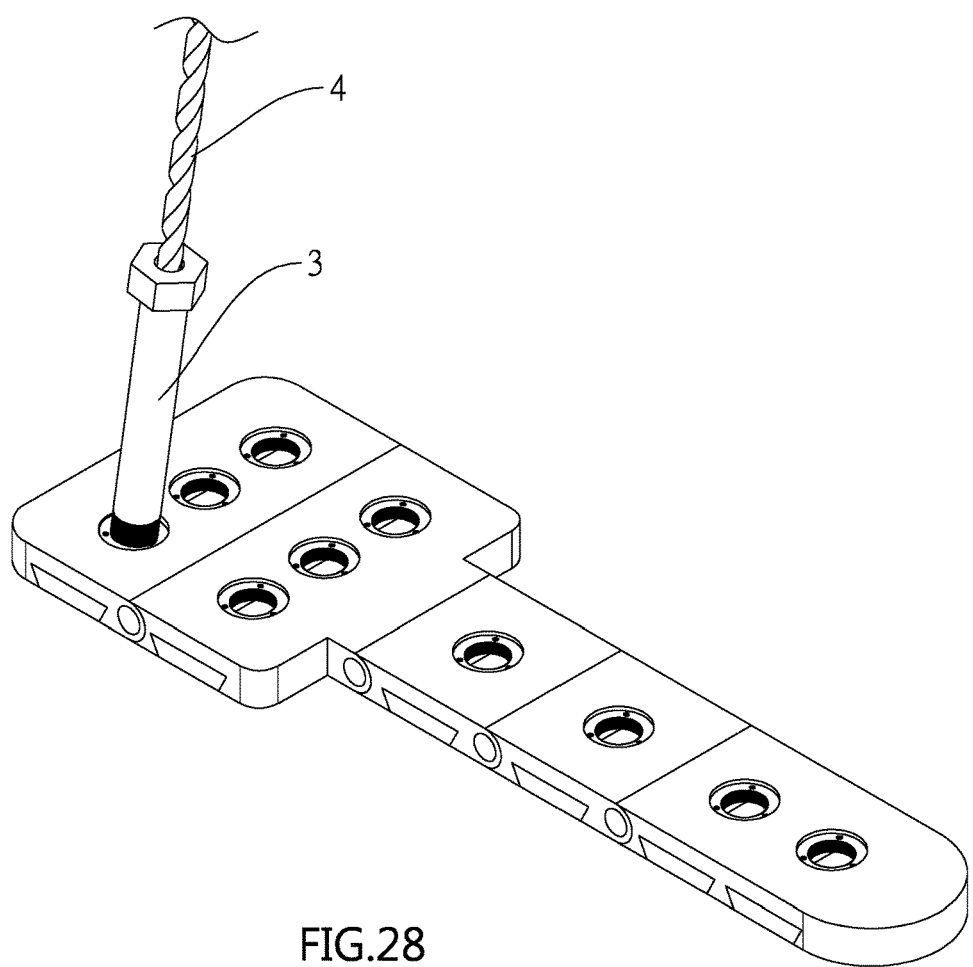
FIG. 28 schematically depicts a tenth step of installing the bone fastening device.
Figure 29:
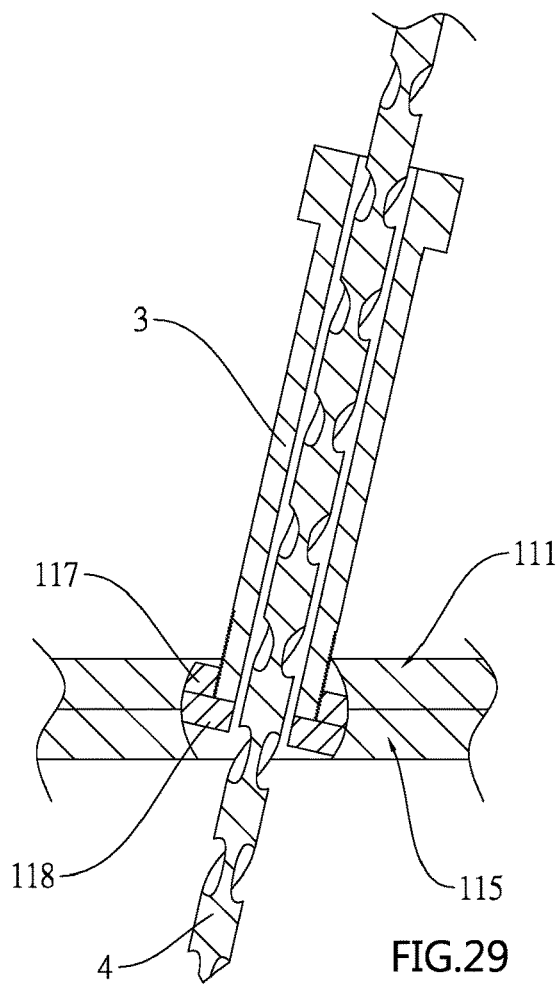
FIG. 29 is a longitudinal sectional view of the left side of FIG. 28.
Figure 30:
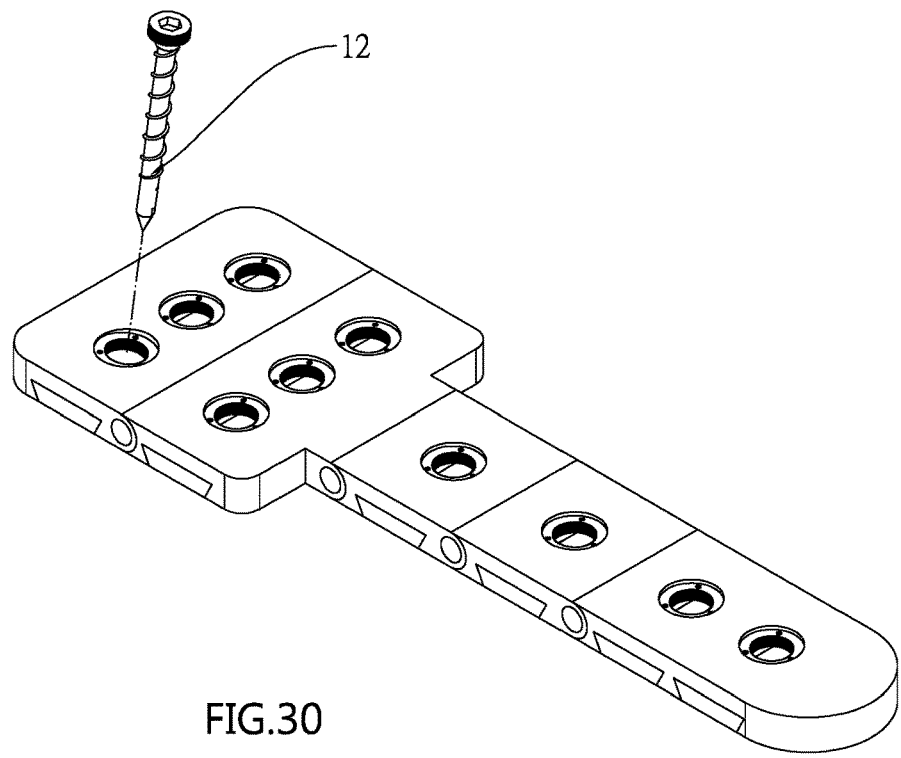
FIG. 30 schematically depicts an eleventh step of installing the bone fastening device.

As shown in FIGS. 22 to 24 in conjunction with FIGS. 3 to 9 specifically, the screw 2 is driven through the threaded hole 111311 of the first hinge section 1113 into the threaded hole 112311 of the second hinge section 1123 to secure the first plate 111 and the second plate 112 together. Next, another screw 2 is driven through the threaded hole 112411 of the third hinge section 1124 into the threaded hole 113311 of the fourth hinge section 1133 to secure the second plate 112 and the third plate 113 together. A ready-to-assemble plate assembly 11 having a first plate 111, a second plate 112 and a third plate 113 are assembled.

Additional steps are required to assemble a ready-to-assemble plate assembly 11 having first plate 111, a second plate 112 and two third plates 113 as detailed below. Still another screw 2 is driven through the knuckle 11341 of the fifth hinge section 1134 of one third plate 113 into the threaded hole 113311 of the fourth hinge section 1133 of the other third plate 113 to secure two third plates 113 together.

An assembly of a ready-to-assemble plate assembly 11 having a first plate 111, a second plate 112 and more than two third plates 113 is similar to the description of the above paragraph.

An assembly of the fourth plate 114 and the adjacent third plate 13 is detailed below. Yet another screw 2 is driven through the knuckle 11341 of the fifth hinge section 1134 of the third plate 113 into the threaded hole 114311 of the sixth hinge section 1143 of the fourth plate 114 to secure the third plate 113 and the fourth plate 114 together.

After the ready-to-assemble plate assembly 11 has been assembled, an angle of one of the first plate 111, the second plate 112, the third plate 113 and the fourth plate 114 with respect to an adjacent one of the first plate 111, the second plate 112, the third plate 113 and the fourth plate 114 can be changed by adjusting the screw 2. Finally, the ready-to-assemble plate assembly 11 is bent to fit on the broken bone based on the radiograph.

As shown in FIGS. 25 to 30 in conjunction with FIGS. 3 to 9 specifically, after the ready-to-assemble plate assembly 11 has been placed on a broken bone and secured thereto by means of a clamp, a tool 3 for guiding a drill bit is threadedly secured to the threaded hole 1171 of the upper half adjustment member 117 of the first plate 111. Next, a wrench is used to fasten the tool 3 and causes the tool 3 to rotate both the upper half adjustment member 117 and the lower half adjustment member 118 until a desired angle is obtained. Next, the positioning bolts 1173 are driven into the threaded positioning holes 1172 and fastened therein. Thus, the upper half adjustment member 117 is pushed upward and the lower half adjustment member 118 is pushed downward until the upper half adjustment member 117 is tightly engaged with the first direction adjustment hole 1111 and the lower half adjustment member 118 is tightly engaged with the first insertion adjustment holes 1151 respectively. Thus, both upper half adjustment member 117 and the lower half adjustment member 118 are fastened (i.e., being not adapted to adjust). Next, a drill is used to drive a drill bit 4 through the tool 3 into the bone until a guide hole having a desired depth is obtained. Next, a measurement tool is used to measure the depth of the guide hole. Next, the tool 3 is removed. Next, a plurality of screws 12 having a desired length are driven into the guide holes respectively until the first external threads 1212 are fastened in the threaded holes 1171 respectively. Also, a threaded hole is formed in the bone by driving the second external thread 1231 into the bone and the second external thread 1231 is fastened therein. Thus, the screws 12 are used to drive the remaining upper half adjustment members 117 associated with the first plate 111 into the bone, thereby finishing the installation of the first plate 111 by means of the screws 12.

Next, the installation of the fourth plate 114 by means of the screws 12 is discussed below. Similar to the above description, the tool 3 for guiding a drill bit is threadedly secured to the threaded hole 1171 of the upper half adjustment member 117 of the fourth plate 114. Next, a wrench is used to fasten the tool 3 and causes the tool 3 to rotate both the upper half adjustment member 117 and the lower half adjustment member 118 until a desired angle is obtained. Next, the positioning bolts 1173 are driven into the threaded positioning holes 1172 and fastened therein. Thus, the upper half adjustment member 117 is pushed upward and the lower half adjustment member 118 is pushed downward until the upper half adjustment member 117 is tightly engaged with the first direction adjustment hole 1111 and the lower half adjustment member 118 is tightly engaged with the first insertion adjustment holes 1151 respectively. Thus, both upper half adjustment member 117 and the lower half adjustment member 118 are fastened (i.e., being not adapted to adjust). Next, the drill is used to drive the drill bit 4 through the tool 3 into the bone until a guide hole having a desired depth is obtained. Next, the measurement tool is used to measure the depth of the guide hole. Next, the tool 3 is removed. Next, a plurality of screws 12 having a desired length are driven into the guide holes respectively until the first external threads 1212 are fastened in the threaded holes 1171 respectively. Also, a threaded hole is formed in the bone by driving the second external thread 1231 into the bone and the second external thread 1231 is fastened therein. Thus, the screws 12 are used to drive the remaining upper half adjustment members 117 associated with the fourth plate 114 into the bone, thereby finishing the installation of the fourth plate 114 by means of the screws 12.

Next, the installation of the second plate 112 by means of the screws 12 is discussed below. Similar to the above description, the tool 3 for guiding a drill bit is threadedly secured to the threaded hole 1171 of the upper half adjustment member 117 of the second plate 112. Next, a wrench is used to fasten the tool 3 and causes the tool 3 to rotate both the upper half adjustment member 117 and the lower half adjustment member 118 until a desired angle is obtained. Next, the positioning bolts 1173 are driven into the threaded positioning holes 1172 and fastened therein. Thus, the upper half adjustment member 117 is pushed upward and the lower half adjustment member 118 is pushed downward until the upper half adjustment member 117 is tightly engaged with the first direction adjustment hole 1111 and the lower half adjustment member 118 is tightly engaged with the first insertion adjustment holes 1151 respectively. Thus, both upper half adjustment member 117 and the lower half adjustment member 118 are fastened (i.e., being not adapted to adjust). Next, the drill is used to drive the drill bit 4 through the tool 3 into the bone until a guide hole having a desired depth is obtained. Next, the measurement tool is used to measure the depth of the guide hole. Next, the tool 3 is removed. Next, a plurality of screws 12 having a desired length are driven into the guide holes respectively until the first external threads 1212 are fastened in the threaded holes 1171 respectively. Also, a threaded hole is formed in the bone by driving the second external thread 1231 into the bone and the second external thread 1231 is fastened therein. Thus, the screws 12 are used to drive the remaining upper half adjustment members 117 associated with the second plate 112 into the bone, thereby finishing the installation of the second plate 112 by means of the screws 12.

Next, the installation of the third plate 113 by means of the screws 12 is discussed below. Similar to the above description, the tool 3 for guiding a drill bit is threadedly secured to the threaded hole 1171 of the upper half adjustment member 117 of the third plate 113. Next, a wrench is used to fasten the tool 3 and causes the tool 3 to rotate both the upper half adjustment member 117 and the lower half adjustment member 118 until a desired angle is obtained. Next, the positioning bolts 1173 are driven into the threaded positioning holes 1172 and fastened therein. Thus, the upper half adjustment member 117 is pushed upward and the lower half adjustment member 118 is pushed downward until the upper half adjustment member 117 is tightly engaged with the first direction adjustment hole 1111 and the lower half adjustment member 118 is tightly engaged with the first insertion adjustment holes 1151 respectively. Thus, both upper half adjustment member 117 and the lower half adjustment member 118 are fastened (i.e., being not adapted to adjust). Next, the drill is used to drive the drill bit 4 through the tool 3 into the bone until a guide hole having a desired depth is obtained. Next, the measurement tool is used to measure the depth of the guide hole. Next, the tool 3 is removed. Next, a plurality of screws 12 having a desired length are driven into the guide holes respectively until the first external threads 1212 are fastened in the threaded holes 1171 respectively. Also, a threaded hole is formed in the bone by driving the second external thread 1231 into the bone and the second external thread 1231 is fastened therein. Thus, the screws 12 are used to drive the remaining upper half adjustment members 117 associated with the third plate 113 into the bone, thereby finishing the installation of the third plate 113 by means of the screws 12.

Finally, after all of the screws 12 have been installed, the clamp is removed. This finishes the installation of the invention.

While the invention has been described in terms of preferred embodiments, those skilled in the art will recognize that the invention can be practiced with modifications within the spirit and scope of the appended claims.

What is claimed is:

1. A bone fastening device comprising a ready-to-assemble plate assembly including a first plate, a second plate, a third plate, a fourth plate, first insertion members, second insertion members, a plurality of upper half adjustment members, and a plurality of lower half adjustment members; and a plurality of screws wherein the first plate includes a plurality of first direction adjustment holes on a top surface, the first direction adjustment holes each having a truncated conic shape; a first groove on a bottom passing through the first direction adjustment holes and being perpendicular thereto; and a first hinge section at a first side and having a knuckle, a threaded hole through the knuckle, and a trough aligned with the threaded hole and communicating therewith;

the second plate and the first plate are joined;

the second plate includes a plurality of second direction adjustment holes on a top surface, the second direction adjustment holes each having a truncated conic shape; a second groove on a bottom passing through the second direction adjustment holes and being perpendicular thereto; a second hinge section at a second side and having a first knuckle, a first threaded hole through the first knuckle, and a first trough aligned with the first threaded hole and communicating therewith; and a third hinge section at a first side and having a second knuckle, a second threaded hole through the second knuckle, and a second trough aligned with the second threaded hole and communicating therewith;

the third plate and the second plate are joined;

the third plate includes a plurality of third direction adjustment holes on a top surface, the third direction adjustment holes each having a truncated conic shape; a third groove on a bottom passing through the third direction adjustment holes and being perpendicular thereto; a fourth hinge section at a second side and having a first knuckle, a first threaded hole through the first knuckle, and a first trough aligned with the first threaded hole and communicating therewith; and a fifth hinge section at a first side and having a second knuckle and a second trough at the second side and passing through the second knuckle;

the fourth plate and the third plate are joined;

the fourth plate includes a plurality of fourth direction adjustment holes on a top surface, the third direction adjustment holes each having a truncated conic shape; two parallel fourth grooves on a bottom each passing through one of the fourth direction adjustment holes and being perpendicular thereto; and a sixth hinge section at a second side and having a knuckle, a threaded hole through the knuckle, and a trough aligned with the threaded hole and communicating therewith;

the first insertion members are inserted into the first groove and the second groove respectively; the first insertion members each includes a plurality of first insertion adjustment holes corresponding to the first direction adjustment holes and the second direction adjustment holes respectively; and the first insertion adjustment holes each has a truncated conic shape;

the second insertion members are inserted into the third groove and the fourth grooves respectively; the second insertion members each includes a plurality of second insertion adjustment holes corresponding to the third direction adjustment hole and the fourth direction adjustment holes respectively; and the second insertion adjustment holes each has a truncated conic shape;

the upper half adjustment members are disposed in the first direction adjustment holes, the second direction adjustment holes, the third direction adjustment holes, and the fourth direction adjustment holes respectively; the upper half adjustment members each is configured to fit in the truncated conic shape inner surface of each of the first direction adjustment holes, the second direction adjustment holes, the third direction adjustment holes, and the fourth direction adjustment holes; and the upper half adjustment members each includes a threaded hole;

the lower half adjustment members each includes a through hole having a diameter less than that of the threaded hole of the upper half adjustment member; and an outer surface of each of the lower half adjustment members is shaped as an inverted truncated cone to allow the lower half adjustment members to be disposed in the first insertion adjustment holes or the second insertion adjustment holes; and the screws each includes a head having a socket and first external threads; a shank having second external threads and a concave tip; and a cylindrical positioning section between the head and the shank, the cylindrical positioning section having a diameter equal to a diameter of the lower half adjustment member; and the head is threadedly fastened in the threaded hole of each of the lower half adjustment members.

2. The bone fastening device of claim 1, wherein a width of the third plate is less than that of the second plate.

3. The bone fastening device of claim 1, wherein a width of the fourth plate is equal to that of the third plate.

4. The bone fastening device of claim 1, wherein the upper half adjustment members each further comprises a plurality of threaded positioning holes.

5. The bone fastening device of claim 4, further comprising a plurality of positioning bolts disposed in the threaded positioning holes respectively.

* * * * *